US011471624B2

(12) United States Patent
Lau et al.

(10) Patent No.: US 11,471,624 B2
(45) Date of Patent: Oct. 18, 2022

(54) CARTRIDGE FOR E-VAPING DEVICE WITH OPEN-MICROCHANNELS

(71) Applicant: Altria Client Services LLC, Richmond, VA (US)

(72) Inventors: Raymond W. Lau, Richmond, VA (US); Ali A. Rostami, Richmond, VA (US); Eric A. Hawes, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 286 days.

(21) Appl. No.: 16/598,278

(22) Filed: Oct. 10, 2019

(65) Prior Publication Data
US 2020/0060346 A1 Feb. 27, 2020

Related U.S. Application Data

(62) Division of application No. 15/192,052, filed on Jun. 24, 2016, now Pat. No. 10,463,077.

(51) Int. Cl.
*A61M 15/06* (2006.01)
*A61M 11/04* (2006.01)
(Continued)

(52) U.S. Cl.
CPC ............. *A61M 15/06* (2013.01); *A24F 40/42* (2020.01); *A24F 40/485* (2020.01);
(Continued)

(58) Field of Classification Search
None
See application file for complete search history.

(56) References Cited

U.S. PATENT DOCUMENTS 2,350,348 A * 6/1944 Gaugler ................ F28D 15/046
62/119
3,234,357 A * 2/1966 Eberhard ................. H05B 3/00
392/403
(Continued)

FOREIGN PATENT DOCUMENTS

CN 1367707 A 9/2002
CN 104039184 A 9/2014
(Continued)

OTHER PUBLICATIONS

European Office Action dated Nov. 4, 2020 for corresponding European Application No. 17732442.3.
(Continued)

*Primary Examiner* — Thor S Campbell
(74) *Attorney, Agent, or Firm* — Harness, Dickey & Pierce, P.L.C.

(57) ABSTRACT

A cartridge for an e-vaping device includes a reservoir configured to hold a pre-vapor formulation and a channel structure that includes a channel surface with one or more open-microchannels. An open-microchannel in the channel structure may be in fluid communication with the reservoir and may transport pre-vapor formulation from the reservoir to a heating element based on capillary action of the pre-vapor formulation through the open-microchannels. The heating element may vaporize the pre-vapor formulation drawn through one or more open-microchannels. The cartridge may be independent of fibrous dispensing interfaces, including one or more wicks. Fabrication of such a cartridge may be simplified, faster, cheaper, some combination thereof, or the like relative to fabrication of a cartridge that includes a fibrous or soft dispensing interface to draw pre-vapor formulation from a reservoir to a heating element.

12 Claims, 11 Drawing Sheets

(51) Int. Cl.
  *F22B 1/28* (2006.01)
  *H05B 1/02* (2006.01)
  *H05B 3/44* (2006.01)
  *A24F 40/42* (2020.01)
  *A24F 40/485* (2020.01)
  *A24F 40/10* (2020.01)
  *A24F 40/30* (2020.01)
  *A24F 40/44* (2020.01)

(52) U.S. Cl.
  CPC ........... *A61M 11/042* (2014.02); *F22B 1/284* (2013.01); *H05B 1/0297* (2013.01); *H05B 3/44* (2013.01); *A24F 40/10* (2020.01); *A24F 40/30* (2020.01); *A24F 40/44* (2020.01)

(56) References Cited

U.S. PATENT DOCUMENTS

| | | | |
|---|---|---|---|
| 4,274,479 A * | 6/1981 | Eastman | F28D 15/046 122/366 |
| 4,989,619 A | 2/1991 | Clearman et al. | |
| 5,402,517 A * | 3/1995 | Gillett | A01M 1/2077 392/386 |
| 5,932,315 A * | 8/1999 | Lum | B29C 65/02 428/172 |
| 6,290,685 B1 | 9/2001 | Insley et al. | |
| 6,293,333 B1 | 9/2001 | Ponnappan et al. | |
| 6,361,752 B1 * | 3/2002 | Demarest | A01M 1/2072 422/306 |
| 6,697,571 B2 * | 2/2004 | Triplett | A01M 1/2077 392/395 |
| 6,997,244 B2 | 2/2006 | Hul-Chun | |
| 7,303,143 B2 * | 12/2007 | Davis | A01M 1/2077 239/145 |
| 7,866,374 B2 | 1/2011 | Hou et al. | |
| 8,528,569 B1 | 9/2013 | Newton | |
| 8,689,805 B2 | 4/2014 | Hon | |
| 8,881,737 B2 | 11/2014 | Collett et al. | |
| 2002/0146540 A1 * | 10/2002 | Johnston | F28D 5/00 428/167 |
| 2002/0181946 A1 * | 12/2002 | Brown | A01M 1/2077 392/390 |
| 2005/0077030 A1 | 4/2005 | Wong | |
| 2007/0240855 A1 | 10/2007 | Hou et al. | |
| 2007/0240858 A1 | 10/2007 | Hou et al. | |
| 2010/0263835 A1 | 10/2010 | Wang | |
| 2011/0146955 A1 * | 6/2011 | Chen | B22F 7/08 165/104.26 |
| 2012/0175084 A1 | 7/2012 | Horng | |
| 2012/0255567 A1 * | 10/2012 | Rose | A61K 9/12 131/273 |
| 2013/0043004 A1 * | 2/2013 | Wang | B21C 37/154 165/104.21 |
| 2014/0069424 A1 * | 3/2014 | Poston | A61M 11/047 128/202.21 |
| 2014/0171281 A1 | 6/2014 | Park et al. | |
| 2014/0251326 A1 | 9/2014 | Terry et al. | |
| 2014/0261487 A1 * | 9/2014 | Chapman | A24F 40/44 131/328 |
| 2014/0261492 A1 | 9/2014 | Kane et al. | |
| 2014/0346689 A1 * | 11/2014 | Dubief | B01F 15/06 261/142 |
| 2015/0090280 A1 | 4/2015 | Chen | |
| 2015/0117842 A1 | 4/2015 | Brammer et al. | |
| 2015/0144145 A1 | 5/2015 | Chang et al. | |
| 2015/0201675 A1 | 7/2015 | Lord | |
| 2015/0276262 A1 * | 10/2015 | Dai | A24F 40/46 392/387 |
| 2015/0320116 A1 | 11/2015 | Bleloch et al. | |
| 2016/0021934 A1 | 1/2016 | Cadieux et al. | |
| 2016/0073693 A1 | 3/2016 | Reevell | |
| 2017/0178884 A1 * | 6/2017 | Murtazin | G01J 3/0267 |
| 2017/0280771 A1 * | 10/2017 | Courbat | B05B 17/0669 |
| 2017/0360092 A1 * | 12/2017 | Althorpe | A61M 11/042 |
| 2017/0367407 A1 * | 12/2017 | Althorpe | A61M 15/06 |

FOREIGN PATENT DOCUMENTS

| | | |
|---|---|---|
| CN | 204048047 U | 12/2014 |
| CN | 104824853 A | 8/2015 |
| CN | 205337593 U | 6/2016 |
| DE | 102014106590 A1 | 11/2015 |
| JP | H02-503522 A | 10/1990 |
| JP | 2756328 B2 | 5/1998 |
| JP | H1133097 A | 2/1999 |
| JP | 2007-99970 A | 4/2007 |
| RU | 2014135392 A | 3/2016 |
| WO | WO-2014/130695 A1 | 8/2014 |
| WO | WO-2015186318 A1 | 12/2015 |
| WO | WO-2016079155 A1 | 5/2016 |

OTHER PUBLICATIONS

European Office Action for corresponding Application No. 17732442.3, dated Jan. 30, 2020.

"Optimization of capillary flow through open microchannel and open micropillar arrays," http://iopscience.iop.org/article/10.1088/0022-3727/49/5/055501/pdf.

"Low-frequency acoustic atomization," http://www98.griffith.edu.au/dspace/bitstream/handle/10072/63737/98246_1.pdf;jsessionid=E5E922961A34890825B5B44B2478DD14?sequence=1.

Written Opinion of the International Preliminary Examining Authority dated Jul. 19, 2018 in International Application No. PCT/EP2015/065605.

Decision to Grant and Search Report dated Aug. 11, 2020 in Russian Application No. 2018142877/12(071529).

Notice of Allowance dated Dec. 6, 2021 issued in corresponding Japanese Patent Application No. 2018-564762.

Chinese Office Action dated Feb. 26, 2021 for corresponding Chinese Application No. 201780037067.4, and English-language translation thereof.

Japanese Office Action dated Jul. 1, 2021 for corresponding Japanese Application No. 2018-564762, and English-language translation thereof.

"Optimization of capillary flowthrough open microchannel and open micropillar arrays," http://iopscience.iop.org/article/10.1088/0022-3727/49/5/055501/pdf, published on Jan. 7, 2016.

"Low-frequency acoustic atomization," http://www98.griffith.edu.au/dspace/bitstream/handle/10072/63737/982461.pdf;jsessionid=E5E922961A34890825B5B44B2478DD14?sequence=1, published in 2014.

International Search Report and Written Opinion dated Sep. 12, 2017 issued in corresponding International Patent Application No. PCT/EP2017/065605.

Korean Office Action dated Aug. 3, 2022 for corresponding Korean Application No. 10-2018-7034146, and English-language translation thereof.

* cited by examiner

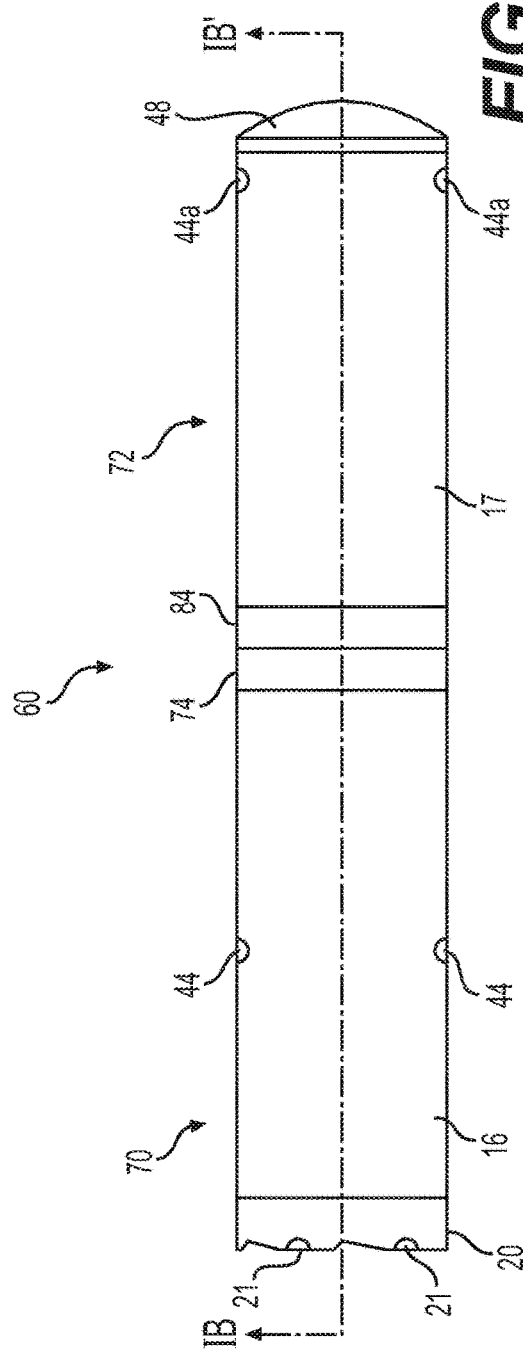
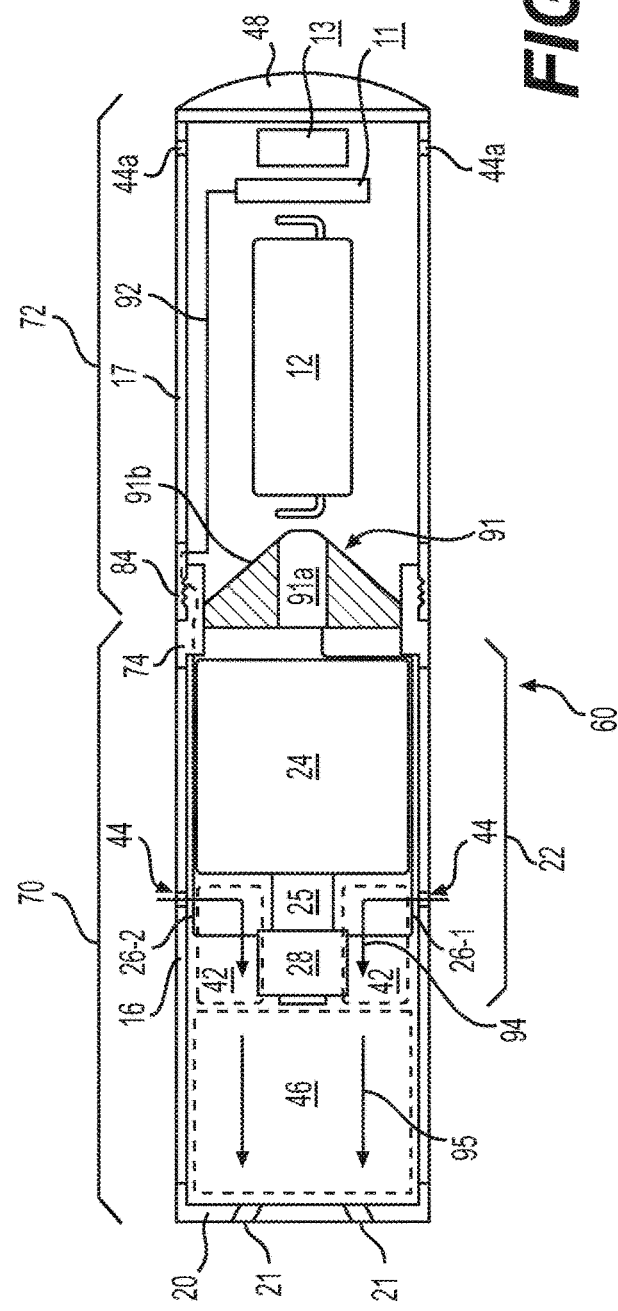

CARTRIDGE FOR E-VAPING DEVICE WITH OPEN-MICROCHANNELS

CROSS-REFERENCE TO RELATED APPLICATION(S)

This application is a Divisional application of U.S. application Ser. No. 15/192,052, filed Jun. 24, 2016, the entire contents of which is incorporated herein by reference.

BACKGROUND

Field

The present disclosure relates to electronic vaping and/or e-vaping devices.

Description of Related Art

E-vaping devices, also referred to herein as electronic vaping devices (EVDs) may be used by adult vapers for portable vaping. Flavored vapors within an e-vaping device may be used to deliver a flavor along with the vapor that may be produced by the e-vaping device.

In some cases, e-vaping devices may hold pre-vapor formulations within a reservoir and may form a vapor based on drawing pre-vapor formulation from the reservoir and applying heat to the drawn pre-vapor formulation to vaporize same.

In some cases, residues may accumulate within an e-vaping device based on the formation of vapor therein. Such residues may be formed based on elements of a pre-vapor formulation material adhering to one or more materials in the e-vaping device. For example, where an e-vaping device includes a soft or fibrous wick to draw pre-vapor formulation from a reservoir to a heating element, residues may accumulate on or in the wick. Residue accumulation may adversely affect e-vaping device performance, based on affecting the rate of vapor formation, increasing the probability of chemical reactions between the residue and one or more elements of the e-vaping device, affecting the elements included in a formed vapor, affecting the amount of vapor formed by the e-vaping device during vapings, some combination thereof, or the like.

In some cases, e-vaping devices may be manufactured via mass-production. Such mass-production may be at least partially automated. In some cases, a complexity of e-vaping devices may have an adverse effect on at least one of the consistency of e-vaping device manufacturing quality, speed of e-vaping device manufacture, and cost of e-vaping device manufacture.

SUMMARY

According to some example embodiments, a cartridge for an e-vaping device may include a reservoir configured to hold a pre-vapor formulation, a channel structure, and at least one heating element. The channel structure may include a channel surface. The channel surface may include a first channel surface portion and an adjacent second channel surface portion. The first channel surface portion may define at least one inner surface of the reservoir. The second channel surface portion may be external to the reservoir. The channel surface may include at least one open-microchannel. The at least one open-microchannel may extend between the first channel surface portion and the second channel surface portion. The channel structure may be configured to draw the pre-vapor formulation from the reservoir to the second channel surface portion based on capillary action of the pre-vapor formulation through the at least one open-microchannel. The at least one heating element may be configured to vaporize the pre-vapor formulation drawn to the second channel surface portion to form a vapor.

The at least one open-microchannel may have a trapezoidal channel cross-section.

The channel structure may include a hydrophilic layer on the channel surface.

The heating element may include a surface heater.

The heating element may be coupled to the second channel surface portion of the channel structure.

The reservoir may include a sealing element configured to substantially seal an interface between the reservoir and the second channel surface portion.

The cartridge may include a plurality of reservoirs. Each of the reservoirs may be configured to hold at least one pre-vapor formulation. The at least one open-microchannel may include a plurality of open-microchannels. Each of the open-microchannels may be in fluid communication with a separate reservoir of the plurality of reservoirs.

The reservoir may be an annular structure configured to hold the pre-vapor within the annular structure. The channel structure may be a disc structure, the first channel surface portion being an outer annular portion of the channel surface and defines a base of the annular structure, and the second channel surface portion being an inner portion of the channel surface. The at least one open-microchannel may extend radially between the outer annular portion of the channel surface and the inner portion of the channel surface. The at least one heating element may be coupled to the inner portion of the channel structure.

The channel structure may include a tubular structure. The channel surface may include an outer surface of the tubular structure. The at least one open-microchannel may extend axially along the outer surface of the tubular structure.

The channel structure may be a molded structure.

The cartridge may include a wicking material in contact with the second channel surface portion and the heating element. The wicking material being configured to draw pre-vapor formulation from the at least one open-microchannel in the second channel surface portion to the heating element.

According to some example embodiments, an e-vaping device may include a cartridge for an e-vaping device and a power supply configured to supply electrical power to the cartridge. The cartridge may include a reservoir configured to hold a pre-vapor formulation, a channel structure, and at least one heating element. The channel structure may include a channel surface. The channel surface may include a first channel surface portion and an adjacent second channel surface portion. The first channel surface portion may define at least one inner surface of the reservoir. The second channel surface portion may be external to the reservoir. The channel surface may include at least one open-microchannel. The at least one open-microchannel may extend between the first channel surface portion and the second channel surface portion. The channel structure may be configured to draw the pre-vapor formulation from the reservoir to the second channel surface portion based on capillary action of the pre-vapor formulation through the at least one open-microchannel. The at least one heating element may be configured to vaporize the pre-vapor formulation drawn to the second channel surface portion to form a vapor.

The at least one open-microchannel may have a trapezoidal channel cross-section.

The channel structure may include a hydrophilic layer on the channel surface.

The heating element may include a surface heater.

The heating element may be coupled to the second channel surface portion of the channel structure.

The reservoir may include a sealing element configured to substantially seal an interface between the reservoir and the second channel surface portion.

The e-vaping device may include a plurality of reservoirs. Each of the reservoirs may be configured to hold at least one pre-vapor formulation. The at least one open-microchannel may include a plurality of open-microchannels. Each of the open-microchannels may be in fluid communication with a separate reservoir of the plurality of reservoirs.

The reservoir may be an annular structure configured to hold the pre-vapor within the annular structure. The channel structure may be a disc structure. The first channel surface portion may be an outer annular portion of the channel surface and define a base of the annular structure. The second channel surface portion may be an inner portion of the channel surface. The at least one open-microchannel may extend radially between the outer annular portion of the channel surface and the inner portion of the channel surface. The at least one heating element may be coupled to the inner portion of the channel structure.

The channel structure may include a tubular structure. The channel surface may include an outer surface of the tubular structure. The at least one open-microchannel may extend axially through the outer surface of the tubular structure.

The channel structure may be a molded structure.

The power supply may include a rechargeable battery.

The cartridge and the power supply may be removably connected together.

The cartridge may further include a wicking material in contact with the second channel surface portion and the heating element. The wicking material may be configured to draw pre-vapor formulation from the at least one open-microchannel in the second channel surface portion to the heating element.

According to some example embodiments, a method may include: drawing a pre-vapor formulation from a reservoir to a heating element through at least one open-microchannel, the at least one open-microchannel including a first portion and a second portion, the first portion being in fluid communication with the reservoir, the second portion being coupled to the heating element; and vaporizing the pre-vapor formulation drawn to the heating element through the at least one open-microchannel to form a vapor.

The method may further include drawing the pre-vapor formulation to the heating element through a plurality of parallel open-microchannels.

The method may further include: drawing a plurality of pre-vapor formulations from a plurality of reservoirs to at least one heating element through a plurality of open-microchannels, each of the open-microchannels being in fluid communication with a separate reservoir of the plurality of reservoirs; and vaporizing the pre-vapor formulations drawn to the at least one heating element through the plurality of open-microchannels to form at least one vapor.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1A is a side view of an e-vaping device according to some example embodiments.

FIG. 1B is a cross-sectional view along line IB-IB' of the e-vaping device of FIG. 1A.

DETAILED DESCRIPTION OF EXAMPLE EMBODIMENTS

Figure 2A:
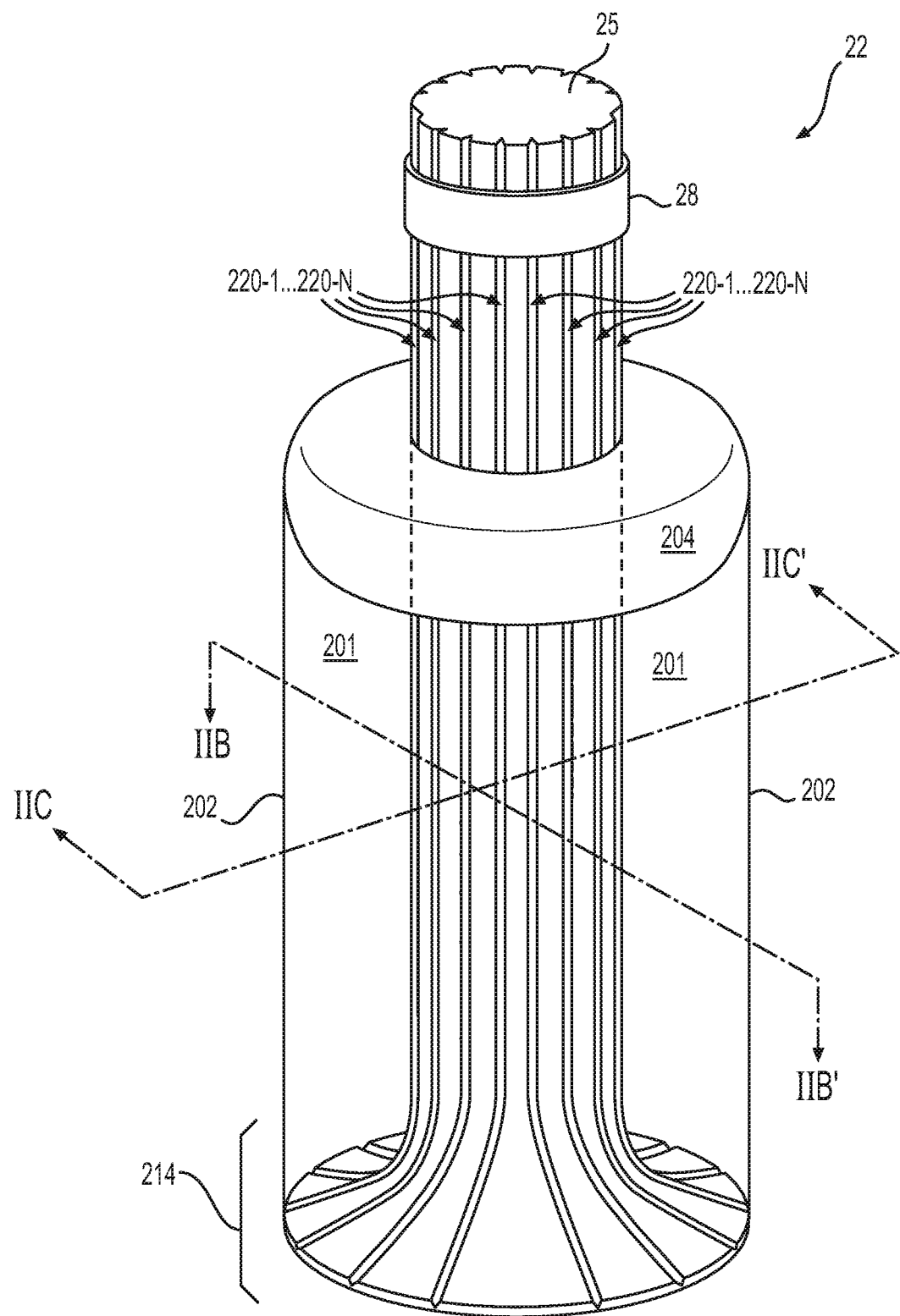
FIG. 2A is a perspective view of a vaporizer assembly according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1A is a side view of an e-vaping device 60 according to some example embodiments. FIG. 1B is a cross-sectional view along line IB-IB' of the e-vaping device of FIG. 1A. The e-vaping device 60 may include one or more of the features set forth in U.S. Patent Application Publication No. 2013/0192623 to Tucker et al. filed Jan. 31, 2013 and U.S. Patent Application Publication No. 2013/0192619 to Tucker et al. filed Jan. 14, 2013, the entire contents of each of which are incorporated herein by reference thereto. As used herein, the term "e-vaping device" is inclusive of all types of electronic vaping devices, regardless of form, size or shape.

Referring to FIG. 1A and FIG. 1B, an e-vaping device 60 includes a replaceable cartridge (or first section) 70 and a reusable power supply section (or second section) 72. The sections 70, 72 may be coupled together at complimentary interfaces 74, 84 of the respective sections 70, 72.

In some example embodiments, the interfaces 74, 84 are threaded connectors. It should be appreciated that an interface 74, 84 may be any type of connector, including, without limitation, a snug-fit, detent, clamp, bayonet, and/or clasp.

As shown in FIG. 1A and FIG. 1B, in some example embodiments, an outlet end insert 20 may be positioned at an outlet end of the cartridge 70. The outlet end insert 20 includes at least one outlet port 21 that may be located off-axis from the longitudinal axis of the e-vaping device 60. One or more of the outlet ports 21 may be angled outwardly in relation to the longitudinal axis of the e-vaping device 60. Multiple outlet ports 21 may be uniformly or substantially uniformly distributed about the perimeter of the outlet end insert 20 so as to substantially uniformly distribute vapor drawn through the outlet end insert 20 during vaping. Thus, as a vapor 95 is drawn through the outlet end insert 20, the vapor may move in different directions.

The cartridge 70 includes an outer housing 16 extending in a longitudinal direction. The power supply section 72 includes an outer housing 17 extending in a longitudinal direction. In some example embodiments, the outer housing 16 may be a single tube housing both the cartridge 70 and the power supply section 72, and the entire e-vaping device 60 may be disposable. The outer housing 16 may have a generally cylindrical cross-section. In some example embodiments, the outer housing 16 may have a generally triangular cross-section along one or more of the cartridge 70 and the power supply section 72. In some example embodiments, the outer housing 16 may have a greater circumference or dimensions at a tip end than at an outlet end of the e-vaping device 60.

Still referring to FIGS. 1A-B, the cartridge 70 includes a vaporizer assembly 22 configured to form a vapor 95 based on vaporization of a pre-vapor formulation. The vaporizer assembly 22 includes at least a reservoir 24, a channel structure 25, and a heating element 28. The reservoir 24 is configured to hold a pre-vapor formulation. The channel structure 25 is configured to draw pre-vapor formulation from the reservoir 24. The heating element 28 is configured to vaporize the drawn pre-vapor formulation to form the vapor 95. The vaporizer assembly 22 will be described further below with reference to at least FIGS. 2A-C, FIG. 3, and FIG. 4.

The reservoir 24 may hold a pre-vapor formulation within an interior of the reservoir 24. The channel structure 25 is coupled to the reservoir 24, such that at least a portion of the channel structure 25 is in fluid communication with the reservoir 24 interior. The channel structure 25 may include one or more materials, including a metal material, a plastic material, some combination thereof, or the like. For example, the channel structure 25 may at least partially or entirely include polytetrafluoroethylene (PTFE). The channel structure 25 may include a hydrophilic material, a moldable material, some combination thereof, or the like. For example, the channel structure 25 may include a hydrophilic injection moldable material. A hydrophilic injection moldable material may include Poly(methyl methacrylate)

(PMMA), polyvinyl alcohol (PVA), polylactic acid (PLA), some combination thereof, or the like.

As discussed further below, the channel structure 25 is configured to draw pre-vapor formulation from the reservoir to one or more portions of the channel structure 25 that are external to the reservoir 24. The channel structure 25 may include one or more open-microchannels that are configure to draw pre-vapor formulation from the reservoir 24 based on capillary action of the pre-vapor formulation in the open-microchannels.

The heating element 28 is positioned proximate to a portion of the channel structure 25 to which pre-vapor formulation may be drawn from the reservoir 24. The heating element 28 may be coupled to the portion of the channel structure 25 to which pre-vapor formulation may be drawn from the reservoir 24. As shown in the example embodiments illustrated in FIG. 1B, the heating element 28 may extend on a surface of the channel structure 25. In some example embodiments, the heating element 28 may extend parallel or transverse (orthogonal, perpendicular, etc.) to a longitudinal axis of the channel structure 25.

The heating element 28 is configured to generate heat. The channel structure 25 is configured to draw pre-vapor formulation from the reservoir 24, such that the pre-vapor formulation may be vaporized from the channel structure 25 based on heating of the channel structure 25 by the heating element 28.

During vaping, pre-vapor formulation may be transferred from the reservoir 24 via capillary action of one or more open-microchannels (not shown in FIGS. 1A-B) of the channel structure 25. The heating element 28 may at least partially surround a portion of the channel structure 25 such that if and/or when the heating element 28 is activated to generate heat, the pre-vapor formulation in the portions of one or more open-microchannels that extend through the portion of the channel structure 25 may be vaporized by the heating element 28 to form a vapor.

In some example embodiments, at least one air inlet port 44 may be formed in the outer housing 16, adjacent to the interface 74 to minimize the probability of an adult vaper's fingers occluding one of the ports and to control the resistance-to-draw (RTD) during vaping. In some example embodiments, the air inlet ports 44 may be machined into the outer housing 16 with precision tooling such that their diameters are closely controlled and replicated from one e-vaping device 60 to the next during manufacture.

In some example embodiments, the air inlet ports 44 may be drilled with carbide drill bits or other high-precision tools and/or techniques. In some example embodiments, the outer housing 16 may be formed of metal or metal alloys such that the size and shape of the air inlet ports 44 may not be altered during manufacturing operations, packaging, and vaping. Thus, the air inlet ports 44 may provide consistent RTD. In some example embodiments, the air inlet ports 44 may be sized and configured such that the e-vaping device 60 has a RTD in the range of from about 40 mm $H_2O$ to about 150 mm $H_2O$.

One or more elements of the cartridge 70 define internal spaces 42 and 46 within the cartridge 70 interior. As shown, the cartridge 70 interior includes spaces 42 that are at least partially defined by the outer housing 16 of the cartridge 70 and one or more elements of the vaporizer assembly 22. The cartridge interior further includes space 46 that is at least partially defined by the outer housing 16, vaporizer assembly 22, and the outlet end insert 20. Internal spaces 42 are each in fluid communication with one or more air inlet ports 44. Internal space 46 is in fluid communication with one or more air inlet ports 21. The internal spaces 42 may be referred to as one or more upstream portions of the cartridge 70 interior. The internal space 46 may be referred to as a downstream portion of the cartridge 70 interior. Air 94 may be drawn into spaces 42 via the one or more air inlet ports 44. Vapor 95 formed by the vaporizer assembly 22 may be released into at least one of spaces 42 and 46. At least the vapor 95 and air 94 may be drawn through the air outlet ports 21 through space 46.

In the example embodiments illustrated in FIGS. 1A-B, the air inlet ports 44 are located downstream of at least a portion of the vaporizer assembly 22. The air inlet ports 44 may be configured to direct air 94 into spaces 42 that are at in fluid communication with a portion of the channel structure 25 at which vapor 95 may be formed. For example, as shown in FIG. 1B, the air inlet ports 44 are positioned upstream of the heating element 28, so that air 94 drawn through the air inlet ports 44 into spaces 42 may pass in fluid communication with a portion of the channel structure 25 that is proximate to the heating element 28. Vapor 95 formed by the vaporizer assembly 22 may mix with the air 94. At least one of the vapor 95 and air 94 may pass downstream, through space 46, to exit the cartridge 70 through one or more of the air outlet ports 21.

In some example embodiments, the cartridge 70 includes a connector element 91. Connector element 91 may include one or more of a cathode connector element and an anode connector element. In the example embodiment illustrated in FIG. 1B, for example, electrical lead 26-1 is coupled to the connector element 91. As further shown in FIG. 1B, the connector element 91 is configured to couple with a power supply 12 included in the power supply section 72. If and/or when interfaces 74, 84 are coupled together, the connector element 91 and power supply 12 may be coupled together. Coupling connector element 91 and power supply 12 together may electrically couple lead 26-1 and power supply 12 together.

In some example embodiments, one or more of the interfaces 74, 84 include one or more of a cathode connector element and an anode connector element. In the example embodiment illustrated in FIG. 1B, for example, electrical lead 26-2 is coupled to the interface 74. As further shown in FIG. 1B, the power supply section 72 includes a lead 92 that couples the control circuitry 11 to the interface 84. If and/or when interfaces 74, 84 are coupled together, the coupled interfaces 74, 84 may electrically couple leads 26-2 and 92 together.

If and/or when interfaces 74, 84 are coupled together, one or more electrical circuits through the cartridge 70 and power supply section 72 may be established. The established electrical circuits may include at least the heating element 28, the control circuitry 11, and the power supply 12. The electrical circuit may include electrical leads 26-1 and 26-2, lead 92, and interfaces 74, 84.

The connector element 91 may include an insulating material 91b and a conductive material 91a. The conductive material 91a may electrically couple lead 26-1 to power supply 12, and the insulating material 91b may insulate the conductive material 91a from the interface 74, such that a probability of an electrical short between the lead 26-1 and the interface 74 is reduced and/or prevented. For example, if and/or when the connector element 91 includes a cylindrical cross-section orthogonal to a longitudinal axis of the e-vaping device 60, the insulating material 91b included in connector element 91 may be in an outer annular portion of the connector element 91 and the conductive material 91a may be in an inner cylindrical portion of the connector element 91, such that the insulating material 91*b* surrounds the conductive material 91*a* and reduces and/or prevents a probability of an electrical connection between the conductive material 91*a* and the interface 74.

Still referring to FIG. 1A and FIG. 1B, the power supply section 72 includes a sensor 13 responsive to air drawn into the power supply section 72 via an air inlet port 44*a* adjacent to a free end or tip end of the e-vaping device 60, at least one power supply 12, and control circuitry 11. The power supply 12 may include a rechargeable battery. The sensor 13 may be one or more of a pressure sensor, a microelectromechanical system (MEMS) sensor, etc.

In the illustrated embodiments shown in FIGS. 1A-B, the sensor 13 and control circuitry 11 are located proximate to a tip end of the power supply section 72. It will be understood that, in some example embodiments, one or more of the sensor 13 and the control circuitry 11 may be located in one or more different locations in the power supply section 72, including one or more locations that are different from the tip end of the power supply section 72. For example, in some example embodiments, one or more of the control circuitry 11 and the sensor 13 may be located proximate to an outlet end of the power supply section 72.

In some example embodiments, the power supply 12 includes a battery arranged in the e-vaping device 60 such that the anode is downstream of the cathode. A connector element 91 contacts the downstream end of the battery. The heating element 28 is connected to the power supply 12 by at least electrical lead 26-1 and connector element 91 if and/or when interfaces 74, 84 are coupled together.

The power supply 12 may be a Lithium-ion battery or one of its variants, for example a Lithium-ion polymer battery. Alternatively, the power supply 12 may be a nickel-metal hydride battery, a nickel cadmium battery, a lithium-manganese battery, a lithium-cobalt battery or a fuel cell. The e-vaping device 60 may be usable by an adult vaper until the energy in the power supply 12 is depleted or in the case of lithium polymer battery, a minimum voltage cut-off level is achieved.

Further, the power supply 12 may be rechargeable and may include circuitry configured to allow the battery to be chargeable by an external charging device. To recharge the e-vaping device 60, a Universal Serial Bus (USB) charger or other suitable charger assembly may be used.

Upon completing the connection between the cartridge 70 and the power supply section 72, the at least one power supply 12 may be electrically connected with the heating element 28 of the cartridge 70 upon actuation of the sensor 13. Air is drawn primarily into the cartridge 70 through one or more air inlet ports 44. The one or more air inlet ports 44 may be located along the outer housing 16, 17 of the first and second sections 70, 72 or at one or more of the coupled interfaces 74, 84.

The sensor 13 may be configured to sense an air pressure drop and initiate application of voltage from the power supply 12 to the heating element 28. As shown in the example embodiment illustrated in FIG. 1B, some example embodiments of the power supply section 72 include a heater activation light 48 configured to glow if and/or when the heating element 28 is activated. The heater activation light 48 may include a light emitting diode (LED). Moreover, the heater activation light 48 may be arranged to be visible to an adult vaper during vaping. In addition, the heater activation light 48 may be utilized for e-vaping system diagnostics or to indicate that recharging is in progress. The heater activation light 48 may also be configured such that the adult vaper may activate and/or deactivate the heater activation light 48 for privacy. As shown in FIG. 1A and FIG. 1B, the heater activation light 48 may be located on the tip end of the e-vaping device 60. In some example embodiments, the heater activation light 48 may be located on a side portion of the outer housing 17.

In addition, the at least one air inlet port 44*a* may be located adjacent to the sensor 13, such that the sensor 13 may sense air flow indicative of vapor being drawn through the outlet end of the e-vaping device. The sensor 13 may activate the power supply 12 and the heater activation light 48 to indicate that the heating element 28 is activated.

Further, the control circuitry 11 may control the supply of electrical power to the heating element 28 responsive to the sensor 13. In some example embodiments, the control circuitry 11 may include a maximum, time-period limiter. In some example embodiments, the control circuitry 11 may include a manually operable switch for an adult vaper to manually initiate vaping. The time-period of the electric current supply to the heating element 28 may be pre-set depending on the amount of pre-vapor formulation desired to be vaporized. In some example embodiments, the control circuitry 11 may control the supply of electrical power to the heating element 28 as long as the sensor 13 detects a pressure drop.

To control the supply of electrical power to a heating element 28, the control circuitry 11 may execute one or more instances of computer-executable program code. The control circuitry 11 may include a processor and a memory. The memory may be a computer-readable storage medium storing computer-executable code.

The control circuitry 11 may include processing circuitry including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 11 may be at least one of an application-specific integrated circuit (ASIC) and an ASIC chip.

The control circuitry 11 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more of the control circuitry mentioned above. Examples of program code include both machine code produced by a compiler and higher level program code that is executed using an interpreter.

The control circuitry 11 may include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a USB flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The control circuitry 11 may be a special purpose machine configured to execute the computer-executable code to control the supply of electrical power to the heating element 28. Controlling the supply of electrical power to the heating element 28 may be referred to herein interchangeably as activating the heating element 28.

Still referring to FIG. 1A and FIG. 1B, if and/or when the heating element 28 is activated, the activated heating element 28 may heat a portion of a channel structure 25 for less than about 10 seconds. Thus, the power cycle (or maximum vaping length) may range in period from about 2 seconds to about 10 seconds (e.g., about 3 seconds to about 9 seconds, about 4 seconds to about 8 seconds or about 5 seconds to about 7 seconds).

The pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol.

In some example embodiments, the pre-vapor formulation is one or more of propylene glycol, glycerin and combinations thereof.

The pre-vapor formulation may include nicotine or may exclude nicotine. The pre-vapor formulation may include one or more tobacco flavors. The pre-vapor formulation may include one or more flavors which are separate from one or more tobacco flavors.

In some example embodiments, a pre-vapor formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid and combinations thereof.

In some example embodiments, a vapor 95 formed at the vaporizer assembly 22 may be substantially free of one or more materials being in a gas phase. For example, the vapor 95 may include one or more materials substantially in a particulate phase and substantially not in a gas phase.

The storage medium of the reservoir 24 may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In some example embodiments, the reservoir 24 may include a filled tank lacking any storage medium and containing only pre-vapor formulation.

The reservoir 24 may be sized and configured to hold enough pre-vapor formulation such that the e-vaping device 60 may be configured for vaping for at least about 200 seconds. The e-vaping device 60 may be configured to allow each vaping to last a maximum of about 5 seconds.

The heating element 28 may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 28 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 28 may include at least one material selected from the group consisting of stainless steel, copper, copper alloys, nickel-chromium alloys, super alloys and combinations thereof. In some example embodiments, the heating element 28 may be formed of nickel-chromium alloys or iron-chromium alloys. In some example embodiments, the heating element 28 may be a ceramic heater having an electrically resistive layer on an outside surface thereof. In some example embodiments, the heating element 28 may include a porous ceramic material. In some example embodiments, the heating element 28 may include one or more resistive elements, including one or more wires, included within a ceramic material, where the ceramic material may include a porous ceramic material.

The heating element 28 may heat a pre-vapor formulation by thermal conduction. Alternatively, heat from the heating element 28 may be conducted to the pre-vapor formulation by means of a heat conductive element or the heating element 28 may transfer heat to the incoming ambient air that is drawn through the e-vaping device 60 during vaping, which in turn heats the pre-vapor formulation by convection.

In some example embodiments, the vaporizer assembly 22 may include a heating element 28 that is a porous material which incorporates a resistance heater formed of a material having a high electrical resistance capable of generating heat quickly.

In some example embodiments, the cartridge 70 may be replaceable. In other words, once one of the flavorant or the pre-vapor formulation of the cartridge is depleted, only the cartridge 70 may be replaced. In some example embodiments, the entire e-vaping device 60 may be disposed once the reservoir 24 is depleted.

In some example embodiments, the e-vaping device 60 may be about 80 mm to about 110 mm long and about 7 mm to about 8 mm in diameter. For example, in some example embodiments, the e-vaping device 60 may be about 84 mm long and may have a diameter of about 7.8 mm.

In some example embodiments, a pre-vapor formulation may include one or more flavorants. A flavorant may include one or more of a natural flavorant or an artificial ("synthetic") flavorant. A flavorant may include one or more plant extracts. In some example embodiments, a flavorant is one or more of tobacco flavor, menthol, wintergreen, peppermint, herb flavors, fruit flavors, nut flavors, liquor flavors, and combinations thereof. In some example embodiments, a flavorant is included in a botanical material. A botanical material may include material of one or more plants. A botanical material may include one or more herbs, spices, fruits, roots, leaves, grasses, or the like. For example, a botanical material may include orange rind material and sweetgrass material. In another example, a botanical material may include tobacco material.

In some example embodiments, the tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, Dark Tobacco, rare tobacco, specialty tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

Figure 2B:
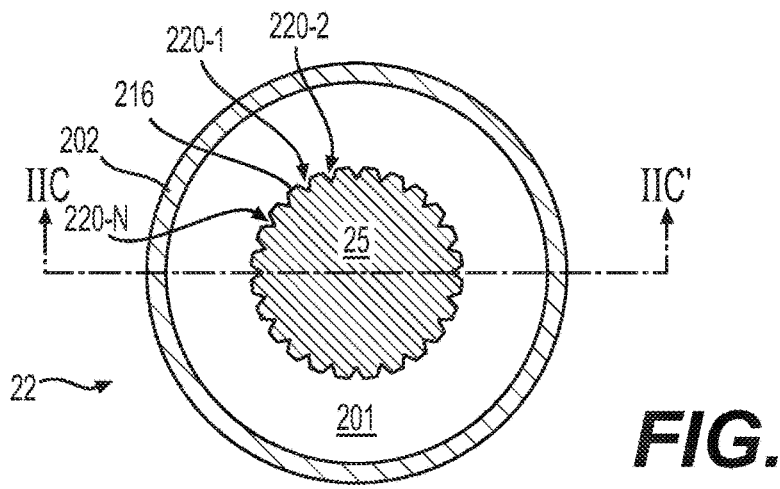
FIG. 2B is a cross-sectional view along line IIB-IIB' of the vaporizer assembly of FIG. 2A.
Figure 2C:
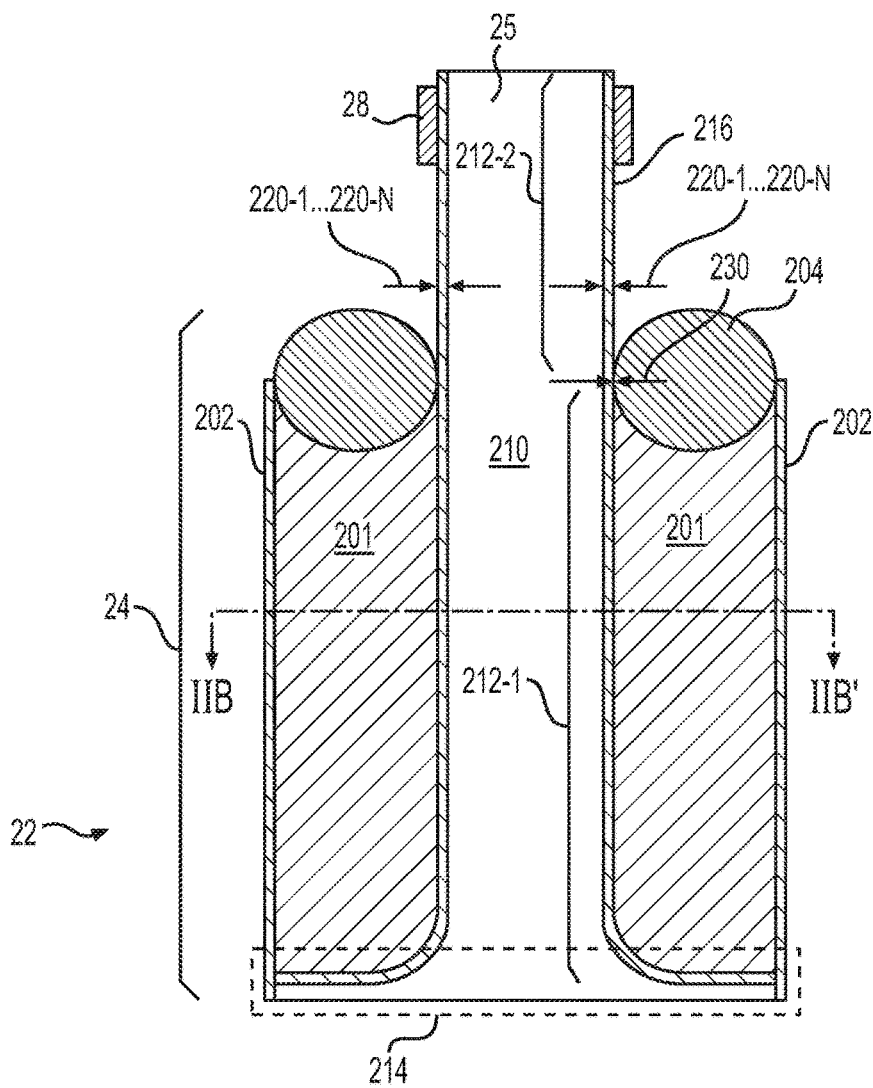
FIG. 2C is a cross-sectional view along line IIC-IIC' of the vaporizer assembly of FIG. 2A.

FIG. 2A is a perspective view of a vaporizer assembly 22 according to some example embodiments. FIG. 2B is a cross-sectional view along line IIB-IIB' of the vaporizer assembly of FIG. 2A. FIG. 2C is a cross-sectional view along line IIC-IIC' of the vaporizer assembly of FIG. 2A. In some example embodiments, the vaporizer assembly 22 illustrated in FIGS. 2A-C may be the vaporizer assembly 22 illustrated in the cartridge 70 of FIGS. 1A-B.

The vaporizer assembly 22 includes a reservoir 24, a channel structure 25, and a heating element 28. The reservoir 24 includes an outer housing 202 and a sealing element 204 (e.g., an O-ring element) that at least partially define an interior 201 of the reservoir 24. The reservoir 24 may hold a pre-vapor formulation in the reservoir interior 201. The outer housing 202, sealing element 204, and at least a portion of channel structure 25 define an interior 201 of reservoir 24. Reservoir 24 holds a pre-vapor formulation within the interior 201.

In some example embodiments, including the example embodiments illustrated in at least FIGS. 2A-C and FIG. 3 below, the channel structure 25 includes a channel surface 216 that includes first and second channel surface portions 212-1 and 212-2, respectively. The first channel surface portion 212-1 of the channel surface 216 defines a boundary of the reservoir interior 201, such that the first channel surface portion 212-1 of the channel surface 216 is in fluid communication with the reservoir interior 201.

The channel structure 25 includes open-microchannels 220-1 to 220-N at the channel surface 216. "N" may be a positive integer having a value of at least one (1). The open-microchannels 220-1 to 220-N extend between the first and second channel portions 212-1 and 212-2. In some example embodiments, one or more of the open-microchannels 220-1 to 220-N is a groove in the channel surface 216. The depth of each open-microchannel 220-1 to 220-N extends, orthogonally to a longitudinal axis of the open-microchannel 220-1 to 220-N, from the channel surface 216 into an interior of the channel structure 25. The open microchannels 220-1 to 220-N may draw pre-vapor formulation from the reservoir 24 based on carrying the pre-vapor formulation through the open-microchannels 220-1 to 220-N from the first channel surface portion 212-1 to the second channel surface portion 212-2.

The portions of the open-microchannels 220-1 to 220-N extending through the first channel surface portion 212-1 are in fluid communication with the reservoir interior 201. The portions of the open-microchannels 220-1 to 220-N extending through the first channel surface portion 212-1 may receive pre-vapor formulation from the reservoir interior 201. The open-microchannels 220-1 to 220-N may carry the received pre-vapor formulation from the first channel surface portion 212-1 to the second channel surface portion 212-2, based on capillary action of the open-microchannels 220-1 to 220-N.

The second channel surface portion 212-2 is restricted from being in direct fluid communication with the reservoir interior 201. The second channel surface portion 212-2 is restricted from being in direct fluid communication with pre-vapor formulation held in the reservoir interior 201. As shown in FIGS. 2A and 2C, the sealing element 204 seals or substantially seals an interface 230 with the channel surface 216, such that pre-vapor formulation flow from the reservoir interior 201 is restricted to flow through the open-microchannels 220-1 to 220-N.

In some example embodiments, including the example embodiments illustrated in FIGS. 2A-C, the vaporizer assembly 22 includes one or more heating elements 28 configured to heat the pre-vapor formulation drawn to the second channel surface portion 212-2 by the open-microchannels 220-1 to 220-N. In the example embodiments shown in FIGS. 2A-C, the one or more heating elements 28 are coupled to the channel structure 25 at the second channel surface portion 212-2.

In some example embodiments, including the example embodiments illustrated in FIGS. 2A-C, the channel structure 25 includes a cylindrical structure 210. The cylindrical structure 210 extends between the reservoir 24 and an exterior of the reservoir 24, such that the cylindrical structure 210 at least partially defines an annular reservoir interior 210 that surrounds the first channel surface portion 212-1. In the example embodiments illustrated in FIGS. 2A-C, the channel structure 25 includes a disc structure 214 that defines a base of the reservoir interior 201. As further shown in FIGS. 2A-C, the channel surface 216 may extend between the cylindrical and disc structures 210 and 214, and the open-microchannels 220-1 to 220-N may extend between the cylindrical and disc structures 210 and 214.

In the example embodiments illustrated in FIGS. 2A-C, the channel structure 25 includes a continuous curve shape (e.g., absent of surface vertices and/or edges) between the cylindrical and disc structures 210 and 214. Such a continuous curve shape may improve pre-vapor formulation transport through the open-microchannels 220-1 to 220-N as the amount of pre-vapor formulation held in the reservoir interior 201 is depleted. For example, as the amount of pre-vapor formulation is depleted, the remaining pre-vapor formulation may form an annular pool surrounding portions of the disc structure 214 such that the pre-vapor formulation remains in fluid communication with open-microchannels 220-1 to 220-N extending along the disc structure 214. As shown, the open microchannels 220-1 to 220-N extend on the cylindrical structure 210 in parallel or substantially in parallel with a longitudinal axis of the cylindrical structure 210, and the open micro-channels 220-1 further extend on the disc structure 214 radially to the outer boundary of the disc structure 214, relative to the cylindrical structure 210.

In some example embodiments, one or more of the cylindrical structure 210 and the disc structure 214 may be absent from the channel structure 25.

In some example embodiments, the channel structure 25 is configured to draw, from the reservoir 24, pre-vapor formulation having one or more certain ranges of intrinsic properties. For example, the channel structures 25 may include one or more open-microchannels 220-1 to 220-N that are configured to draw a pre-vapor formulation based on capillary action of the open-microchannels 220-1 to 220-N if and/or when the pre-vapor formulation has one or more particular intrinsic properties.

Such intrinsic properties may include viscosity of the pre-vapor formulation. For example, in some example embodiments, one or more of the open-microchannels 220-1 to 220-N are configured to draw, based on capillary action of the one or more open-microchannels 220-1 to 220-N, a pre-vapor formulation that has a viscosity ranging from about 1 centipoise to about 60 centipoise.

Such intrinsic properties may include material composition of the pre-vapor formulation. For example, in some example embodiments, one or more of the open-microchannels 220-1 to 220-N is configured to draw, based on capillary action of the one or more open-microchannels 220-1 to 220-N, a pre-vapor formulation that includes a mixture of 80% glycerol and 20% propylene glycol by mass.

In some example embodiments, a channel structure 25 may be configured to include one or more open-microchannels 220-1 to 220-N through implementation of one or more open-microchannel formation processes. Such processes may be implemented by one or more of an operator and a machine device. The machine device may implement such processes based on executing one or more instances of computer-executable program instructions that are stored on one or more instances of non-transitory computer-readable storage media.

In some example embodiments, the channel structure 25 is a molded structure that is molded to include one or more of the open-microchannels 220-1 to 220-N, such that the open-microchannels 220-1 to 220-N are formed concurrently with the formation of the channel structure 25 according to the mold via which the channel structure 25 is formed. For example, the channel structure 25 may be a molded PTFE structure. In some example embodiments, the channel structure may be formed through a three-dimensional (3D) printing process.

In some example embodiments, the channel structure 25 is a cast structure that includes the open-microchannels 220-1 to 220-N, such that the open-microchannels 220-1 to 220-N are formed concurrently with the formation of the channel structure 25 according to the cast via which the channel structure 25 is formed.

In some example embodiments, the open-microchannels 220-1 to 220-N are formed through removing one or more portions of a channel structure 25. Such formation may include "cutting," "etching," "grinding," some combination thereof, or the like to form one or more open-microchannels 220-1 to 220-N in one or more surfaces of the channel structure 25.

Figure 3:
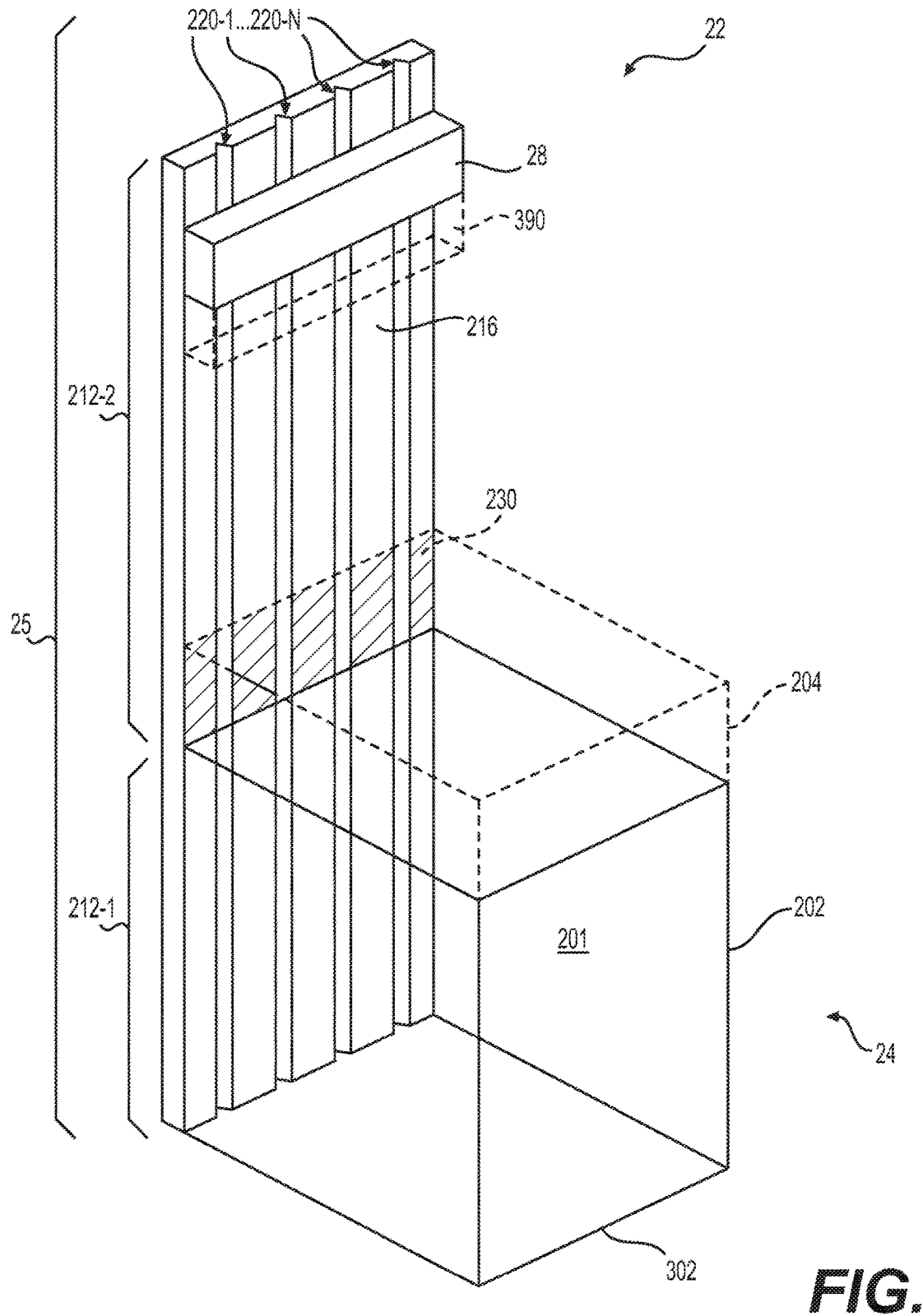
FIG. 3 is a perspective view of a vaporizer assembly according to some example embodiments.

FIG. 3 is a perspective view of a vaporizer assembly 22 according to some example embodiments. In some example embodiments, the vaporizer assembly 22 illustrated in FIG. 3 may be the vaporizer assembly 22 included in the cartridge 70 of FIGS. 1A-B.

Referring to FIG. 3, a vaporizer assembly 22 may include a planar or substantially planar channel structure 25 that at least partially defines a boundary ("surface") of a reservoir interior 201 and extends beyond the reservoir 24.

As shown in FIG. 3, a planar channel structure 25 includes a channel surface 216 having first and second channel surface portions 212-1 and 212-2. The first and second channel surface portions 212-1 and 212-2 may be at least partially defined by exposure to the reservoir interior 201. The first channel surface portion 212-1 is a portion of the channel surface 216 that is in direct fluid communication with the reservoir interior 201, where the reservoir interior 201 is at least partially defined by the channel structure 25, outer housing 202, and base 302. The second channel surface portion 212-2 is a portion of the channel surface 216 that is restricted from direct fluid communication with the reservoir interior 201. The first and second channel portions 212-1 and 212-2 may be defined by interface 230 between a sealing element 204 and the channel surface 216. The sealing element 204 may seal or substantially seal the interface 230, such that pre-vapor formulation flow from the reservoir interiors 201 is restricted to flow through one or more of the open-microchannels 220-1 to 220-N that extend between the first and second channel surface portions 212-1 and 212-2.

The channel structure 25 includes one or more open-microchannels 220-1 to 220-N that are configured to draw pre-vapor formulation from the reservoir interior 201. The open-microchannels 220-1 to 220-N extend between the first and second channel surface portion 212-1 and 212-2. The open-microchannels 220-1 to 220-N may draw pre-vapor formulation from the reservoir interior 201 to the second channel surface portion based on capillary action of the pre-vapor formulation through the open-microchannels 220-1 to 220-N.

As shown in FIG. 3, some example embodiments of the vaporizer assembly 22 include a heating element 28 that is coupled to the second channel surface portion 212-2. The heating element 28 may heat pre-vapor formulation drawn to the second channel surface portion 212-2 by the open-microchannels 220-1 to 220-N. The heating element 28 may thereby vaporize the drawn pre-vapor formulation to form a vapor 95.

In some example embodiments, the vaporizer assembly 22 includes a wicking material 390 that is in contact with one or more portions of the second channel surface portion 212-2 and the heating element 28. The wicking material 390 may include a fibrous wicking material. The wicking material 390 may be in fluid communication with one or more open-microchannels 220-1 to 220-N in the second channel surface portion 212-2. The wicking material 390 may be in fluid communication with the heating element 28 and with the one or more open-microchannels 220-1 to 220-N.

The wicking material 390 may couple the one or more open-microchannels 220-1 to 220-N to the heating element 28. In some example embodiments, the wicking material 390 may draw pre-vapor formulation from the one or more open-microchannels 220-1 to 220-N toward the heating element 28, such that the pre-vapor formulation in the wicking material 390 is in fluid communication with the heating element 28. The pre-vapor formulation drawn from the open-microchannels 220-1 to 220-N by the wicking material 390 may be heated and vaporized by the heating element 28.

Examples of suitable materials of wicking material 390 may be, but not limited to, glass, ceramic- or graphite-based materials. The wicking material 390 may have any suitable capillary drawing action to accommodate pre-vapor formulations having different physical properties such as density, viscosity, surface tension and vapor pressure.

Figure 4A:
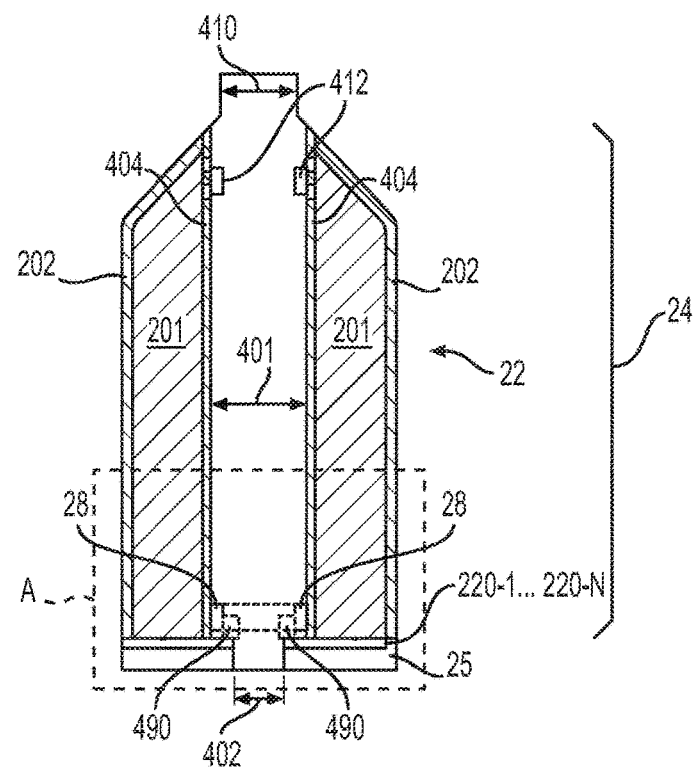
FIG. 4A is a cross-sectional view of a vaporizer assembly according to some example embodiments.
Figure 4B:
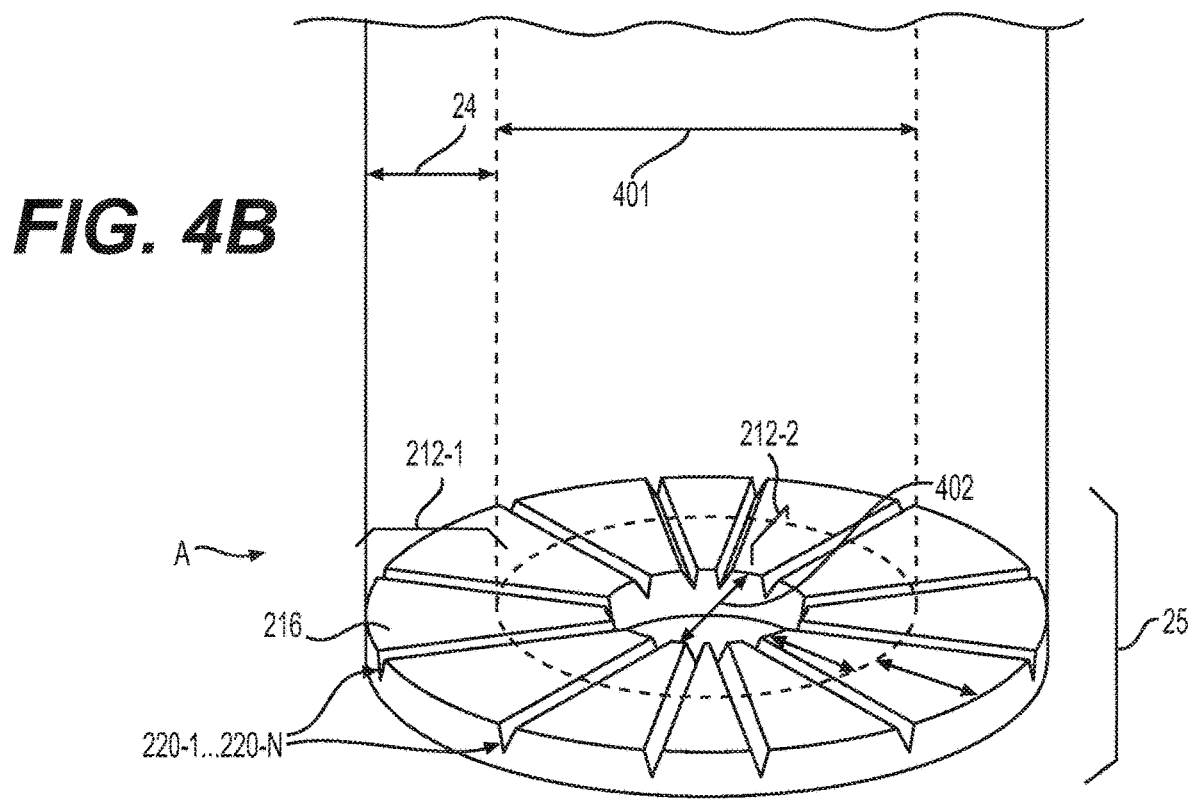
FIG. 4B is a perspective view of section A of the vaporizer assembly of FIG. 4A.

FIG. 4A is a cross-sectional view of a vaporizer assembly according to some example embodiments. FIG. 4B is a perspective view of section A of the vaporizer assembly of FIG. 4A. In some example embodiments, the vaporizer assembly 22 illustrated in FIGS. 4A-B may be the vaporizer assembly 22 included in the cartridge 70 of FIGS. 1A-B.

Referring to FIGS. 4A-B, in some example embodiments, a vaporizer assembly 22 includes a reservoir that is an annular structure configured to hold the pre-vapor within the annular structure, the vaporizer assembly 22 further includes a channel structure 25 that is a disc structure, the channel structure 25 includes a first channel surface portion 212-1 that is an outer annular channel surface portion of the channel surface 216 and defines a base of the annular structure of the reservoir 24, and the channel structure 25 includes a second channel surface portion 212-2 that is an inner channel surface portion of the channel surface 216. The channel structure 25 may include one or more open-microchannels 220-1 to 220-2 that extend radially between the outer annular channel surface portion 212-1 and the inner channel surface portion 212-2. In addition, the vaporizer assembly 22 may include a heating element 28 that is coupled to the inner channel surface portion 212-2.

In the example embodiments illustrated in FIGS. 4A-B, the vaporizer assembly 22 includes a disc channel structure 25 that defines a base of the vaporizer assembly 22. The disc channel structure 25 has an upper surface that is the channel surface 216. As shown in FIGS. 4A-B, the channel surface 216 includes open-microchannels 220-1 to 220-N that extend radially from an inner portion of the disc structure of the channel structure 25.

In the example embodiments illustrated in FIGS. 4A-B, the vaporizer assembly 22 includes a cylindrical outer housing 202 and an inner tube 404 that define an annular reservoir 24 therebetween. The inner tube 404 further defines a cylindrical interior space 401 within the inner tube 404. As shown, the outer housing 202 and inner tube 404 may be coupled together at an upper portion of the vaporizer assembly 22 to define an upper boundary of the reservoir 24. In some example embodiments, a gasket (not shown in FIGS. 4A-B) may be coupled to both the inner tube 404 and the outer housing 202 to define the upper end of the reservoir 24, where the upper end is an opposite end of the reservoir 24, relative to an end of the reservoir 24 that is at least partially defined by the disc channel structure 25.

In the example embodiments illustrated in FIGS. 4A-B, the inner tube 404 and outer housing 202 are coupled to the disc channel structure 25, such that a first channel surface portion 212-1 of the channel surface 216 defines a base boundary of the reservoir 24. The first channel surface portion 212-1 of the channel surface 216 is an annular outer portion of the channel surface 216. The first channel surface portion 212-1 of the channel surface 216 is in fluid communication with the interior of the reservoir 24. The portions of the open-microchannels 220-1 to 220-N that extend through the first channel surface portion 212-1 may receive pre-vapor formulation held in the reservoir 24.

As shown in FIGS. 4A-B, the inner tube 404 partitions the channel surface 216 between first and second channel surface portions 212-1 and 212-2. The open-microchannels 220-1 to 220-N may extend radially between the first and second channel surface portions 212-1 and 212-2. The open-microchannels 220-1 to 220-N may draw pre-vapor formulation from the annular reservoir 24 structure to the second channel surface portion 212-2. The second channel surface portion 212-2 shown in FIG. 4A is in fluid communication with the interior space 401.

In the example embodiments illustrated in FIGS. 4A-B, channel structure 25 includes an opening 402 that extends through the inner portion of the channel structure 25, such that the channel structure 25 is a ring structure. The opening 402 may be an air inlet port. The vaporizer assembly 22 may be configured to draw air into the interior space 401 through the opening 402.

In the example embodiments illustrated in FIGS. 4A-B, the vaporizer assembly 22 includes one or more heating elements 28 that are coupled to a surface that at least partially defines the interior space 401. As shown in FIG. 4A, the heating element 28 may be coupled to the inner tube 404. In some example embodiments, the heating element 28 may be coupled to one or more portions of the second channel surface portion 212-2 of the channel surface 216. The heating element 28 may be configured to generate heat to heat pre-vapor formulation drawn to the second channel surface portion 212-2 of the channel surface 216 by the open-microchannels 220-1 to 220-N such that a vapor is formed in the interior space 401.

In the example embodiments illustrated in FIGS. 4A-B, the vaporizer assembly 22 includes an opening 410 that defines an upper end of the interior space 401. The opening 410 may be at an opposite end of the interior space 401, relative to the end of the interior space 401 that is at least partially defined by the channel structure 25. Vapor formed at the channel structure 25, through vaporization of pre-vapor formulation drawn to the second channel surface portion 212-2 of the channel surface 216, may be drawn through the interior space 401 to exit the vaporizer assembly 22 through the opening 410. In some example embodiments, vapor formed at the second channel surface portion 212-2 may be entrained in air drawn into the interior space 401 through opening 402. The mixture of air and entrained vapor may be drawn through the interior space 401 and away from opening 402 towards and through the opening 410.

In the example embodiments illustrated in FIGS. 4A-B, the vaporizer assembly 22 includes one or more vents 412 that extend through the inner tube 404 between the interior space 401 and the reservoir 24. In some example embodiments, the one or more vents 412 may be pressure-relief vents configured to release one or more fluids (liquids, gasses, etc.) from the reservoir 24 into the interior space 401 if and/or when an internal pressure within the reservoir is equal to or greater than a particular threshold pressure.

In some example embodiments, the vaporizer assembly 22 includes a wicking material 490 that is in contact with one or more portions of the second channel surface portion 212-2 and the heating element 28. The wicking material 490 may include a fibrous wicking material. The wicking material 490 may be in fluid communication with one or more open-microchannels 220-1 to 220-N in the second channel surface portion 212-2. The wicking material 490 may be in fluid communication with the heating element 28 and with the one or more open-microchannels 220-1 to 220-N.

The wicking material 490 may couple the one or more open-microchannels 220-1 to 220-N to the heating element 28. In some example embodiments, the wicking material 490 may draw pre-vapor formulation from the one or more open-microchannels 220-1 to 220-N toward the heating element 28, such that the pre-vapor formulation in the wicking material 490 is in fluid communication with the heating element 28. The pre-vapor formulation drawn from the open-microchannels 220-1 to 220-N by the wicking material 490 may be heated and vaporized by the heating element 28.

Examples of suitable materials of wicking material 490 may be, but not limited to, glass, ceramic- or graphite-based materials. The wicking material 490 may have any suitable capillary drawing action to accommodate pre-vapor formulations having different physical properties such as density, viscosity, surface tension and vapor pressure.

Figure 5:
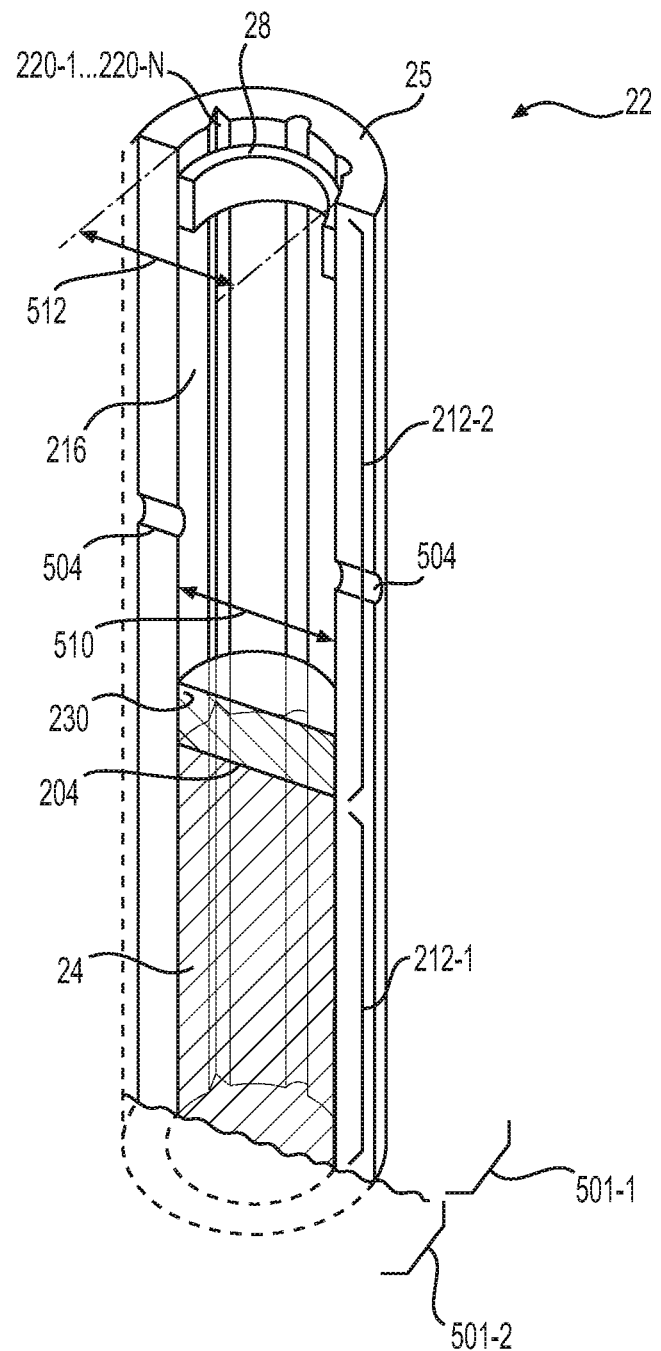
FIG. 5 is a perspective cross-sectional view of a vaporizer assembly according to some example embodiments.

FIG. 5 is a perspective cross-sectional view of a vaporizer assembly according to some example embodiments. In some example embodiments, the vaporizer assembly 22 illustrated in FIG. 5 may be the vaporizer assembly 22 included in the cartridge 70 of FIGS. 1A-B.

Referring to FIG. 5, in some example embodiments, the vaporizer assembly 22 includes a channel structure 25 that at least partially encloses a reservoir 24, such that a channel surface 216 of the channel structure 25 is an inner surface of the channel structure 25. In addition, a first channel surface portion 212-1 may at least partially define a boundary of the reservoir 24 interior.

As shown in FIG. 5, the channel structure 25 may be a hollow cylindrical structure that defines an interior space 510 having an opening 512 at one end and bounded by the inner surface 216 of the hollow cylindrical structure. Open-microchannels 220-1 to 220-N may extend between the first and second channel surface portions 212-1 and 212-2 bounding the interior space 510.

The reservoir 24 may be defined by at least the first channel surface portion 212-1. The reservoir 24 may further be defined by a sealing element 204 that seals or substantially seals the interior space 510 at interface 230. The sealing element 204 may thus partition the interior space 510 into a first section, bounded by the first channel surface portion 212-1 of the channel surface 216, and a second section, bounded by the second channel surface portion 212-2 of the channel surface 216. The first section may define the reservoir 24. The sealing element 204 may restrict pre-vapor formulation flow from the reservoir 24 to flow through one or more of the open-microchannels 220-1 to 220-N that extend between the first and second channel surface portions 212-1 and 212-2.

In the example embodiments of the vaporizer assembly 22 illustrated in FIG. 5, the channel structure 25 includes one or more air inlet ports 504 that extend between an exterior of the channel structure 25 and the interior space 510. The air inlet ports 504 may direct air into the interior space 510. Such air directed into the interior space may be drawn from the interior space 510 through the opening 512 at an end of the channel structure 25.

As shown in FIG. 5, open-microchannels 220-1 to 220-N may draw pre-vapor formulation from the first channel surface portion 212-1 that defines a boundary of the reservoir 24 to the second channel surface portion 212-2 that defines a boundary of the open interior space 510.

In the example embodiments of the vaporizer assembly 22 illustrated in FIG. 5, the heating element 28 is coupled to the second channel surface portion 212-2. The heating element 28 may extend around the inner surface 216, as shown in FIG. 5. As further shown, the open-microchannels 220-1 to 220-N may extend through the second channel surface portion 212-2 to be in fluid communication with the heating element 28. If and/or when pre-vapor formulation is drawn from the reservoir 24 to at least the second channel surface portion 212-2 by the open-microchannels 220-1 to 220-N, the heating element 28 may heat the pre-vapor formulation to form a vapor in the interior space 510 bounded by the second channel surface portion 212-2. As further shown in FIG. 5, the heating element 28 may be positioned closer to the opening 512 than the distance between the air inlet ports 504 and the opening 512. Thus, pre-vapor formulation vaporized by the heating element 28 may be drawn through the opening 512 by air that is drawn into the interior space 510 through the one or more air inlet ports 504.

In some example embodiments, the channel structure 25 illustrated in FIG. 5 is at least a part of the outer housing 16 of the cartridge 70 illustrated in FIGS. 1A-B. The air inlet ports 504 may be the air inlet ports 44 illustrated in FIGS. 1A-B.

FIG. 6A, FIG. 6B, FIG. 6C, and FIG. 6D are cross-sectional views of open-microchannels according to some example embodiments. In some example embodiments, the open-microchannels 220-1 illustrated in FIGS. 6A-D may be the open-microchannel 220-1 included in any of the example embodiments of channel structures 25 included herein, including the channel structure 25 illustrated in FIG. 1B.

Referring to FIGS. 6A-D, in some example embodiments, one or more of the open-microchannels 220-1 to 220-N in a channel structure 25 may have one or more various dimensions, cross-sectional areas, and/or cross sectional area shapes. The dimensions, cross sectional areas, and/or cross sectional area shapes of one or more open-microchannels 220-1 to 220-N may be based on one or more properties of the pre-vapor formulations that may be carried by the open-microchannels 220-1 to 220-N, respectively.

Figure 6A:
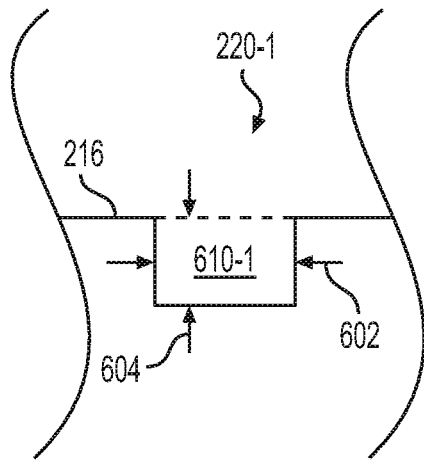
FIG. 6A, FIG. 6B, FIG. 6C, and FIG. 6D are cross-sectional views of open-microchannels according to some example embodiments.

Referring to FIG. 6A, an open-microchannel 220-1 may have a rectangular cross-sectional area shape, such that the open-microchannel 220-1 has a certain width 602, a certain depth 604, and a certain cross-sectional area 610-1. The open-microchannel 220-1 may be configured to transport a given pre-vapor formulation at one or more flow rates based on one or more of the width 602, depth 604, cross-sectional area 610-1, and cross sectional area shape of the given open-microchannel 220-1.

Referring to Table 1, below, open-microchannels 220-1 to 220-N may have one or more various widths and depths. Such open-microchannels 220-1 to 220-N may include rectangular open-microchannels 220-1, as shown in FIG. 6A. As shown, the width of a rectangular open-microchannel may range, inclusively, from about 100 micrometers to about 300 micrometers. As also shown, the depth of open-microchannels 220-1 may range, inclusively, from about 150 micrometers to about 300 micrometers. It will be understood that the open-microchannel dimensions illustrated in Table 1 may be dimensions of open-microchannels 220-1 having non-rectangular cross-sectional area shapes, as described further below.

TABLE 1

Open-Microchannel Dimensions

| Microchannel Size | Width (μm) | Depth (μm) | Cross-Sectional Area (m$^2$) |
|---|---|---|---|
| "Small" microchannel | 100 | 150 | $1.5 \times 10^{-8}$ |
| "Medium" microchannel | 200 | 300 | $6.0 \times 10^{-8}$ |
| "Large" microchannel | 300 | 300 | $9.0 \times 10^{-8}$ |

In some example embodiments, a rate at which pre-vapor formulation is drawn by an open-microchannel 220-1 may be based on one or more of the dimensions and cross sectional area of the open-microchannel 220-1. For example, an individual "small" open-microchannel 220-1 may be configured to draw a given pre-vapor formulation at a rate of approximately 0.01 microliters per second. In another example, an individual "medium" open-microchannel 220-1 may be configured to draw the given pre-vapor formulation at a rate of approximately 0.06 microliters per second. In another example, an individual "large" open-microchannel 220-1 may be configured to draw the given pre-vapor formulation at a rate of approximately 0.09 microliters per second.

In some example embodiments, the quantity of open-microchannels 220-1 to 220-N included in a channel structure 25 may be inversely proportional to one or more of the dimensions and cross sectional area of the open-microchannels 220-1 to 220-N. For example, a channel structure 25 that includes a plurality of "large" open-microchannels (300 µm wide and 300 µm deep) may have a smaller quantity of open-microchannels 220-1 to 220-N than a channel structure 25 that includes a plurality of "small" open-microchannels (100 µm wide and 150 µm deep).

Accordingly, in some example embodiments a total rate at which pre-vapor formulation is drawn by a channel structure 25 may be based on one or more of the dimensions and cross sectional area of the open-microchannels 220-1 to 220-N included in the channel structure 25.

For example, a channel structure 25 that includes multiple "small" open-microchannels 220-1 to 220-N may be configured to draw pre-vapor formulation at a total rate of about 0.5 micro-liters/sec. In another example, a channel structure 25 that includes multiple "large" open-microchannels 220-1 to 220-N may be configured to draw pre-vapor formulation at a total rate of about 4.0 micro-liters/sec.

Figure 6B:
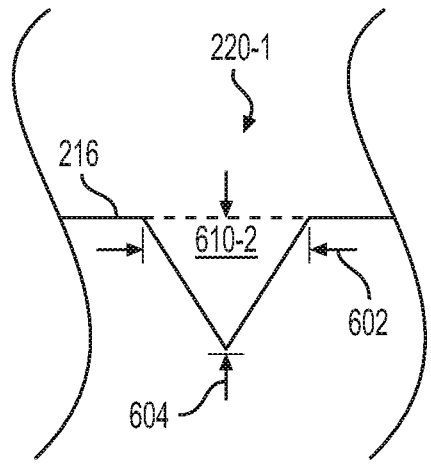

Referring to FIG. 6B, an open-microchannel 220-1 may have a triangular cross-sectional area shape, such that the open-microchannel 220-1 has a certain width 602, a certain depth 604, and a certain triangular cross-sectional area 610-2. While the example embodiments illustrated in FIG. 6B illustrate an open-microchannel having an equilateral triangular cross-sectional area 610-2, it will be understood that the open-microchannel 220-1 may have one or more various triangular cross-sectional area shapes, including an isosceles triangular shape, a right-triangular shape, and a scalene triangular shape. The open-microchannel 220-1 may be configured to transport a given pre-vapor formulation at one or more flow rates based on one or more of the width 602, depth 604, cross-sectional area 610-2, and cross sectional area shape of the given open-microchannel. Referring back to Table 1, the triangular open-microchannel 220-1 may, in some example embodiments, have a width 602 that is equal to one of the widths included in Table 1. Still referring to Table 1, the triangular open-microchannel 220-1 may, in some example embodiments, have a depth that is equal to one of the depths included in Table 1.

Figure 6C:
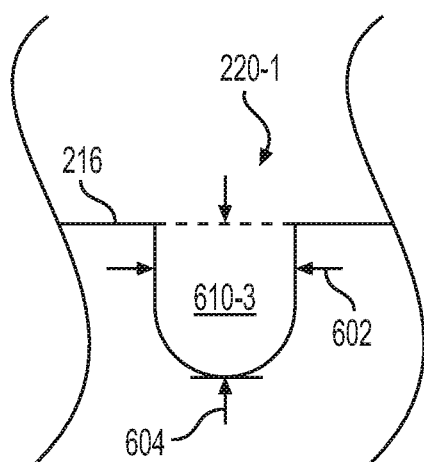

Referring to FIG. 6C, an open-microchannel 220-1 may have a parabolic cross-sectional area shape, such that the open-microchannel 220-1 has a certain width 602, a certain depth 604, and a certain parabolic cross-sectional area 610-3. While the example embodiments illustrated in FIG. 6C illustrate an open-microchannel having a semi-circular cross-sectional area 610-3, it will be understood that the open-microchannel 220-1 may have one or more various parabolic cross-sectional area shapes. The open-microchannel 220-1 may be configured to transport a given pre-vapor formulation at one or more flow rates based on one or more of the width 602, depth 604, cross-sectional area 610-3, and cross sectional area shape of the given open-microchannel. Referring back to Table 1, the parabolic open-microchannel 220-1 may, in some example embodiments, have a width 602 that is equal to one of the widths included in Table 1. Still referring to Table 1, the parabolic open-microchannel 220-1 may, in some example embodiments, have a depth that is equal to one of the depths included in Table 1.

Figure 6D:
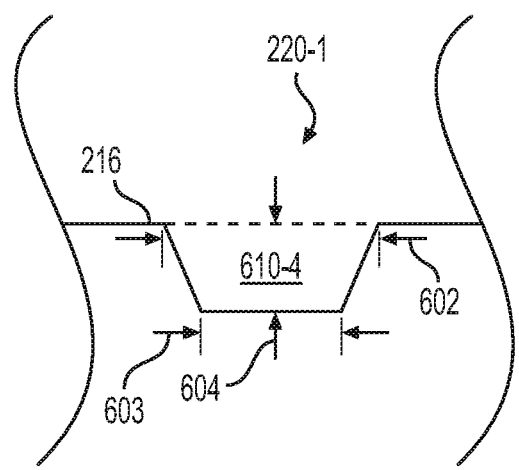

Referring to FIG. 6D, an open-microchannel 220-1 may have a trapezoidal cross-sectional area shape, such that the open-microchannel 220-1 has a certain first width 602, a certain second width 603, a certain depth 604, and a certain trapezoidal cross-sectional area 610-4. In some example embodiments, the first width 602 may be greater than the second width 603. The first width 602 may be greater than the second width 603 to simplify formation of the open-microchannel 220-1. The open-microchannel 220-1 may be configured to transport a given pre-vapor formulation at one or more flow rates based on one or more of the width 602, depth 604, cross-sectional area 610-3, and cross sectional area shape of the given open-microchannel. Referring back to Table 1, the trapezoidal open-microchannel 220-1 may, in some example embodiments, have a first width 602 that is equal to one of the widths included in Table 1. Still referring to Table 1, the trapezoidal open-microchannel 220-1 may, in some example embodiments, have a second width 603 that is equal to one of the widths included in Table 1. Still referring to Table 1, the trapezoidal open-microchannel 220-1 may, in some example embodiments, have a depth that is equal to one of the depths included in Table 1.

Figure 7:
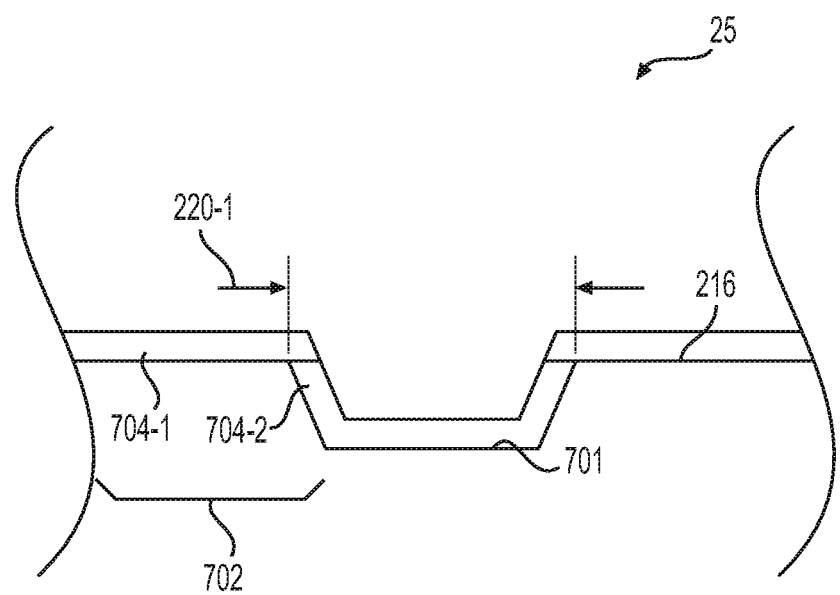
FIG. 7 is a cross-sectional view of an open-microchannel and a hydrophilic layer according to some example embodiments.

FIG. 7 is a cross-sectional view of an open-microchannel and a hydrophilic layer according to some example embodiments. In some example embodiments, the channel surface 216 and open-microchannel 220-1 illustrated in FIG. 7 may be the channel surface 216 and open-microchannel 220-1 included in any of the example embodiments of channel structures 25 included herein, including the channel structure 25 illustrated in FIG. 1B.

As described above, in some example embodiments, the channel structure 25 may include a hydrophilic material. Referring to FIG. 7, in some example embodiments, a channel structure 25 may include a hydrophilic layer 702 on one or more of the channel surface 216 and one or more open-microchannels 220-1 to 220-N. In some example embodiments, the hydrophilic layer 702 may include a layer of one or more materials. For example, the hydrophilic layer 702 may include polyethylene glycol (PEG). The hydrophilic layer 702 may include a PEG coating on one or more of the channel surface 216 and one or more open-microchannels 220-1 to 220-N. In some example embodiments, the hydrophilic layer 702 may be applied to one or more of the channel surface 216 and one or more open-microchannels 220-1 to 220-N according to one or more grafting processes. In some example embodiments, a plasma activation process may be implemented with regard to one or more of the channel surface 216 and one or more open-microchannels 220-1 to 220-N, through plasma processing, such that the one or more of the channel surface 216 and one or more open-microchannels 220-1 to 220-N is configured to be hydrophilic. The one or more of the channel surface 216 and one or more open-microchannels 220-1 to 220-N may retain a plasma activated state if and/or when the one or more of the channel surface 216 and one or more open-microchannels 220-1 to 220-N is in contact with a fluid. Plasma activation, through plasma processing, may include removal of weak boundary layers from the one or more of the channel surface 216 and one or more open-microchannels 220-1 to 220-N, cross-linking of surface molecules in one or more of the channel surface 216 and one or more open-microchannels 220-1 to 220-N, generation of polar groups in one or more of the channel surface 216 and one or more open-microchannels 220-1 to 220-N, some combination thereof, or the like.

In some example embodiments, including the example embodiments illustrated in FIG. 7, the hydrophilic layer 702 is on both at least a portion of the channel surface 216 and the one or more microchannel surfaces 701 of the open-microchannel 220-1. As shown in FIG. 7, the hydrophilic layer 702 may have a first layer portion 704-1 that is on the channel surface 216 and a second layer portion 704-2 that is on the one or more microchannel surfaces 701.

A hydrophilic layer 702 on the channel structure 25 may configure the channel structure 25 to draw pre-vapor formulation through the open-microchannels 220-1 to 220-N at an improved rate. For example, the hydrophilic layer 702 may improve transport of a pre-vapor formulation through the open-microchannel 220-1 based on improved capillary action of the pre-vapor formulation through the open-microchannel 220-1.

In some example embodiments, the first layer portion 704-1 may be absent from the channel structure 25, such that the hydrophilic layer 702 is restricted to portion 704-2 that is on the microchannel surfaces 701 and is absent from the channel surface 216. The first layer portion 704-1 may be removed subsequent to application of the hydrophilic layer 702 on both the channel surface 216 and the microchannel surfaces 701. For example, the hydrophilic layer 702 may be applied according to one or more various layer application methods (coating, deposition, etc.). The first portion 704-1 of the layer may be removed according to one or more layer removal methods (e.g., etching, grinding, etc.), such that the second layer portions 704-2 remains.

Figure 8:
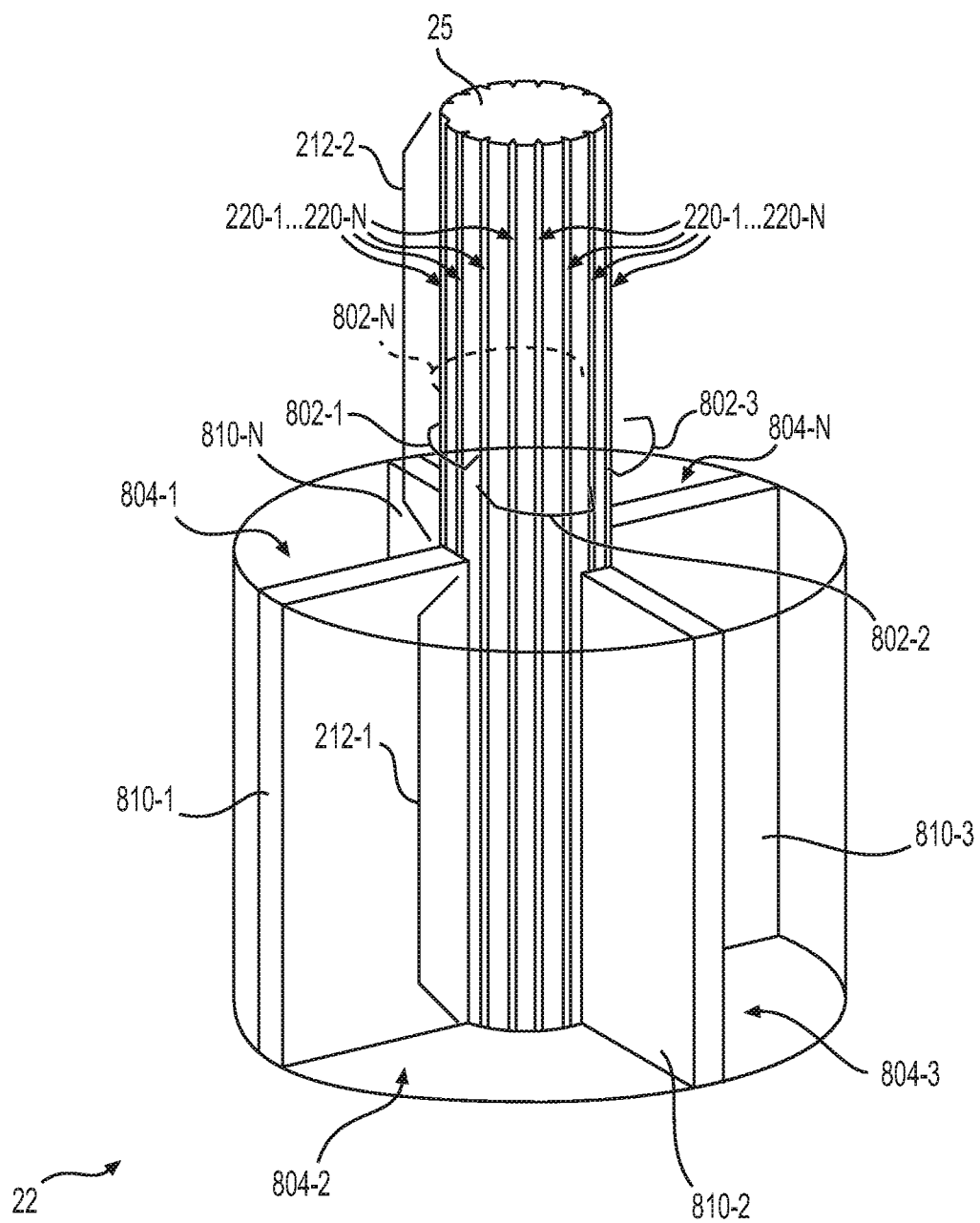
FIG. 8 is a perspective view of a vaporizer assembly according to some example embodiments.

FIG. 8 is a perspective view of a vaporizer assembly 22 according to some example embodiments. In some example embodiments, the vaporizer assembly 22 illustrated in FIG. 8 may be the vaporizer assembly 22 included in the cartridge 70 of FIGS. 1A-B.

Referring to FIG. 8, a vaporizer assembly 22 may include multiple reservoirs 804-1 to 804-N. Each reservoir 804-1 to 804-N may hold a different pre-vapor formulation. The vaporizer assembly 22 may include one or more partitions 810-1 to 810-N that each separate at least two reservoirs 804-1 to 804-N.

As shown in FIG. 8, the channel structure 25 may at least partially define the boundaries of each of the reservoirs 804-1 to 804-N. The channel structures 25 may include multiple channel surface portions 212-1 that are each in fluid communication with a separate reservoir of the reservoirs 804-1 to 804-N. As shown in FIG. 8, for example, a cylindrical channel structure 25 may define a portion of the side boundary of each of the reservoirs 804-1 to 804-N, such that the channel structure 25 includes multiple separate first channel surface portions 212-1 of the channel surface 216, and each separate first channel surface portion 212-1 is in fluid communication with a separate reservoir 804.

In some example embodiments, including the example embodiments illustrated in FIG. 8, the channel structure 25 includes multiple sets 802-1 to 802-N of open-microchannels 220-1 to 220-N. Each separate set 802-1 to 802-N may include at least one open-microchannel of the open-microchannels 220-1 to 220-N. Each separate set 802-1 to 802-N of open-microchannels extends through a separate first channel surface portion 212-1 of the channel surface. Thus, each separate set 802-1 to 802-N of open-microchannels may be at least partially in fluid communication with a different reservoir 804-1 to 804-N. Thus, each separate set 802-1 to 802-N of open-channel microchannels may be configured to draw pre-vapor formulation from a different reservoir 804-1 to 804-N.

If and/or when two or more of the reservoirs 804-1 to 804-N hold different pre-vapor formulations, separate sets 802-1 to 802-N of open-microchannels may draw different pre-vapor formulations from the different reservoirs 804-1 to 804-N, respectively.

Separate sets 802-1 to 802-N of open-microchannels may have different dimensions, properties, etc. For example, the set 802-1 may include a certain quantity of microchannels that have a certain width, a certain depth, and a certain cross-sectional area shape. In another example, the set 802-2 may include a separate quantity of open-microchannels, relative to the open-microchannels included in the set 802-1. The set 802-2 may include one or more open-microchannels that have one or more of a separate width, a separate depth, and a separate cross-sectional area shape, relative to the open-microchannels included in the set 802-1. In another example, the set 802-1 of open-microchannels may include a hydrophilic layer on the surfaces of the open-microchannels, and a hydrophilic layer may be absent from the set 802-2 of open-microchannels.

Separate sets 802-1 to 802-N of open-microchannels may have different dimensions, properties according to different pre-vapor formulations that may be held in the reservoirs 804-1 to 804-N, respectively. In some example embodiments, separate sets 802-1 to 802-N of open-microchannels may have different dimensions, properties according to different pre-vapor formulation flow rates associated with the separate, respective reservoirs 804-1 to 804-N to which the separate sets 802-1 to 802-N of open-microchannels are in fluid communication.

The vaporizer assembly 22 may include one or more heating elements 28 (not shown in FIG. 8) that may be configured to vaporize pre-vapor formulation drawn from one or more of the reservoirs 804-1 to 804-N through one or more sets of open-microchannels 220-1 to 220-N. In some example embodiments, an individual heating element 28 may be configured to vaporize multiple pre-vapor formulations drawn from separate, respective reservoirs 804-1 to 804-N through separate, respective sets 802-1 to 802-N of open-microchannels.

FIG. 9A, FIG. 9B, FIG. 9C, and FIG. 9D are perspective views of vaporizer assemblies according to some example embodiments. In some example embodiments, one or more of the vaporizer assemblies 22 illustrated in FIGS. 9A-D may be the vaporizer assembly 22 illustrated in the cartridge 70 of FIGS. 1A-B. Referring to FIGS. 9A-D, a vaporizer assembly 22 may include a channel structure 25 that has a cylindrical structure.

Figure 9A:
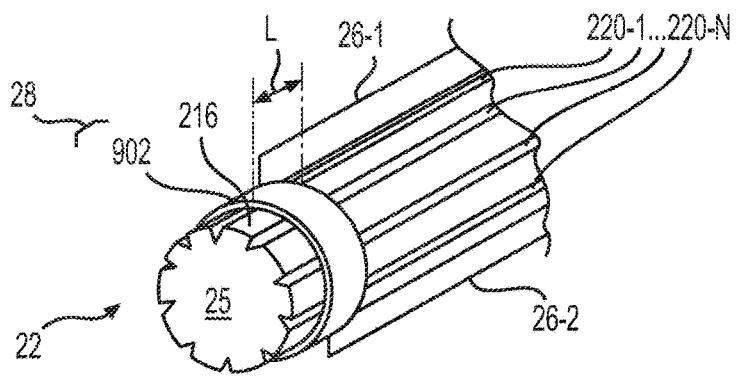
FIG. 9A, FIG. 9B, FIG. 9C, and FIG. 9D are perspective views of vaporizer assemblies according to some example embodiments.

Referring to FIG. 9A, a vaporizer assembly 22 may include a heating element 28 that includes a surface heater 902. The surface heater 902 may contact at least a portion of the channel surface 216 of the channel structure 25. The surface heater 902, in some example embodiments, at least partially defines an enclosure of a portion of one or more open-microchannels 220-1 to 220-N. The one or more open-microchannels may thus include a closed-microchannel portion. As shown in the example embodiments illustrated in FIG. 9A, the closed-microchannel portions of the open-microchannels 220-1 to 220-N may be defined by the channel structure 25 and the surface heater 902.

In some example embodiments, the surface heater 902 at least partially fills a cross-sectional area of one or more open-microchannels 220-1 to 220-N, thereby establishing a flow terminus for pre-vapor formulation that may flow through the one or more open-microchannels 220-1 to 220-N. Pre-vapor formulation that may flow through the open-microchannels 220-1 to 220-N may flow in contact with the surface heater 902.

In some example embodiments, a surface heater 902 may include one or more of a planar heater, a conformal heater, some combination thereof, or the like. In the example embodiments illustrated in FIG. 9A, for example, the surface heater 902 is a conformal heater that surrounds a portion of the channel structure 25.

In some example embodiments, including the embodiments illustrated in FIG. 9A, the heater 902 may be at least partially wrapped about a circumference of a cylindrical structure of the channel structure 25. Such a heater 902 may extend along at least a portion of a length ("L") of the channel structure 25.

In some example embodiments, the surface heater 902 may be in contact with a portion of an outer circumference of the cylindrical structure of channel structure 25. The conformal planar surface heater 902 may extend along a particular proportion of the structure 25 circumference. A conformal planar surface heater 902 may include a heater element arranged in one or more patterns. The one or more patterns may include a wave pattern. The wave pattern may include a sinusoidal wave pattern of heater elements. The sinusoidal waves included in the sinusoidal wave pattern may be spaced apart by a particular distance.

As shown in the example embodiments illustrated in FIG. 9A, the surface heater 902 may include a conformal ring surface heater that extends completely around the circumference of the channel structure 25. The conformal ring surface heater 902 may include a heater element arranged in one or more patterns. The one or more patterns may include a wave pattern. The wave pattern may include a sinusoidal wave pattern of heater elements. The sinusoidal waves included in the sinusoidal wave pattern may be spaced apart by a particular distance. The conformal ring surface heater may extend along a particular proportion of a length "L" of the channel structure 25. In some example embodiments, the heaters are resistive heaters.

A surface heater, including a conformal heater, planar heater, etc., may be a flexible heater. A flexible heater may be a thick film heater constructed of one or more thick films. A flexible heater may include one or more resistive traces arranged in a pattern of resistive traces on a substrate. The substrate may be a flexible substrate. The flexible heater may include one or more adhesive layers configured to bond the flexible heater to a surface, including a gel formulation surface. An adhesive layer may include a pressure sensitive adhesive (PSA) layer.

A thick film heater may be a printed thick film heater where a pattern of resistive traces included in the thick film heater is a pattern of an ink material printed on a film substrate layer. The ink material may include a resistive ink. The film may include a PSA layer applied to the substrate on which the ink is printed. The thick film heater may include another layer laminated to the substrate and ink layer with the PSA layer. In some example embodiments, a film layer includes a 0.05-inch thick thermoplastic or thermoset polymer substance, where the substance is configured to exhibit thermal conductivity while providing electrical insulation. For example, the film layer may be formed of polyester or polyimide. An additional layer of PSA may be applied to an exterior surface of the thick film heater, such that the thick film heater may be bonded directly to the channel structure 25, thereby enhancing thermal transfer between the heater 902 and the channel structure 25. Heat may be transferred to pre-vapor formulation carried in open-microchannels 220-1 to 220-N through conduction through the channel structure 25.

In some example embodiments, a thick film heater includes a substrate constructed from one or more of polyester, polyethylene, polyvinyl chloride, thermoset laminate, polyethylene napthalate, polyimide, silicone rubber, or some combination thereof. A thick film heater may include a PSA layer formed of one or more of acrylic materials or silicone materials. A thick film heater may have a minimum width of 6 mm. A thick film heater may have a dielectric strength of up to 1500 VAC. A thick film heater may have a watt density of up to 25 W/square inches. A thick film heater may have an operating voltage of up to about 277 VAC or 277 VDC. A thick film heater may have an overall maximum operating temperature of about 482 degrees Celsius.

In some example embodiments, a flexible heater includes one or more of a single-sided heater, a double-sided heater, a multi-layer heater, a rigid-flex heater, and some combination thereof. A single sided heater includes a single heating element layer, which may be a resistive trace. A double sided heater includes two heating element layers. A flexible heater may include a sculptured heating element, where a sculptured heating element has variable thickness through the heater structure. A sculptured heating element may have bare metal portions exposed from the heater structure. A rigid-flex heater includes at least one rigid layer and at least one flexible layer. A flexible heater may have a thickness of at least 0.004 inches. A flexible heater may include at least two parallel traces having different resistances. The parallel traces may be separately, selectively activated to provide different rates of heating. A flexible heater may have a bend radius that is about 10 times the thickness of the flexible heater. One or more heating elements in the flexible heater may be radiused resistive traces. Where a flexible heater includes multiple layers of parallel heating elements, the separate layers may have a staggered configuration, thereby providing augmented flexibility of the flexible heater.

In some example embodiments, a surface heater 902 includes a solid state heater. A solid state heater may include a heating element that is one or more sets of resistive traces. A solid state heater may be a ceramic solid state heater. A solid state heater may be constructed from a combination of platinum and at least one ceramic material. A solid state heater may have a three-dimensional heating element geometric structure. A solid state heater may include multiple separate heating elements. A solid state heater may include an aluminum nitride ceramic material. A solid state heater may include a ceramic material and one or more internal resistance traces. A resistance trace may be constructed from tungsten. A solid state heater may include Aluminum nitride (ALN) ceramic and tungsten. Where a solid state heater includes ALN and tungsten, the tungsten metal and ALN may be bonded via chemical bonding. An oxide phase may be inter-diffused between the ALN and Tungsten metal.

A solid state heater may have a linear coefficient of expansion per degree Celsius of about $4.3 \times 10^{-6}$. A solid state heater may have a DC breakdown of 14 KV/mil, a Young's Modulus of about 322 GPa, a flexural strength of about 350 MPa, a thermal conductivity of about 130 W/m-k at 200 degrees Celsius, a thermal conductivity of about 180 W/m-k at room temperature, a dielectric loss of about $1.2 \times 10^{-4}$ at room temperature and a frequency of 1 mhz, a dielectric constant of about 8.5-8.7 at room temperature and a frequency of 1 mhz, and some combination thereof. In some example embodiments, a planar heater includes a planar metal surface heater.

Figure 9B:
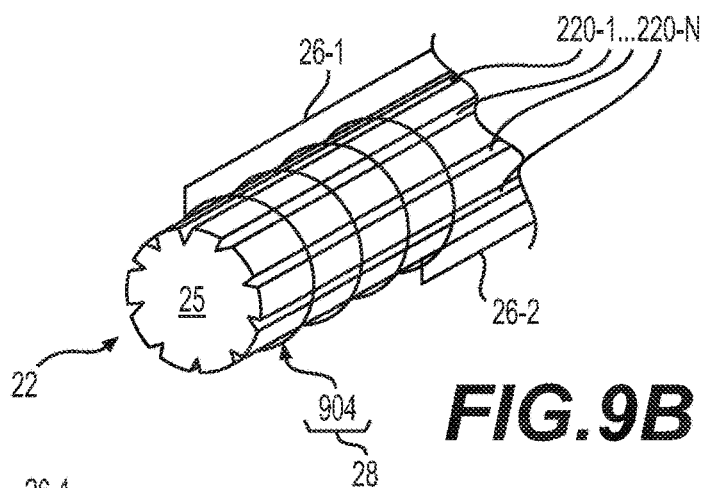

Referring to FIG. 9B, a vaporizer assembly 22 may include a heating element 28 that includes a coil heater 904. The coil heater 904 may be wrapped about the circumference of the channel surface 216 of the channel structure 25. The coil heater 904, in some example embodiments, may include a particular quantity of coils around the channel structure 25. The coil heater 904 may be spaced a particular distance from the surface of the cylindrical body 50. The coils may be spaced a particular distance apart.

The coil heater 904 may include a wire coil. The wire coil may include a metal wire. The wire coil may extend fully or partially along the length of the dispensing interface. The wire coil may further extend fully or partially around the circumference of the channel structure 25. In some example embodiments, the wire coil may be isolated from direct contact with the channel structure 25.

Figure 9C:
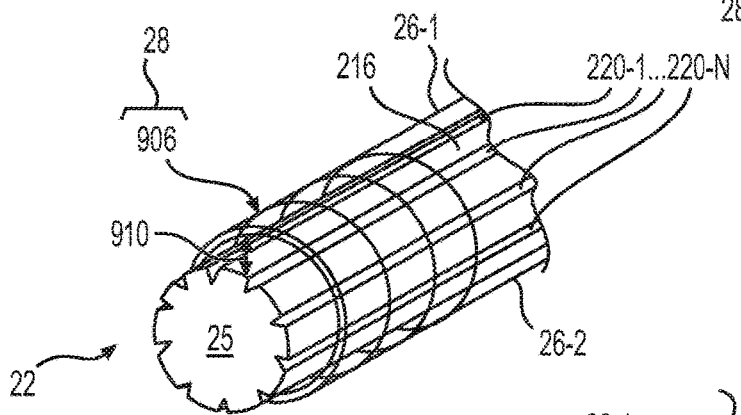

Referring to FIG. 9C, a vaporizer assembly 22 may include a heating element 28 that includes an inductive coil heater 906. The inductive coil heater 906 may not contact a channel surface 216 of the channel structure 25. The inductive coil heater 906 may be referred to as being isolated from contacting a surface 216 of the channel structure 25. The inductive coil heater 902 may be configured to heat the pre-vapor formulation carried in the open-microchannels 220-1 to 220-N to a temperature sufficient to vaporize the pre-vapor formulation. The inductive coil heater 906 may include a particular quantity of coils around the channel structure 25. The inductive coil heater 906 coils may be spaced a particular distance 910 from the surface 216 of the channel structure 25.

A heating element 28 that includes an inductive coil heater 906 may be configured to apply inductive heating by transferring energy from a primary coil (not shown in FIG. 9C) to the coil heater 906, where the coil heater 906 is a secondary coil.

Figure 9D:
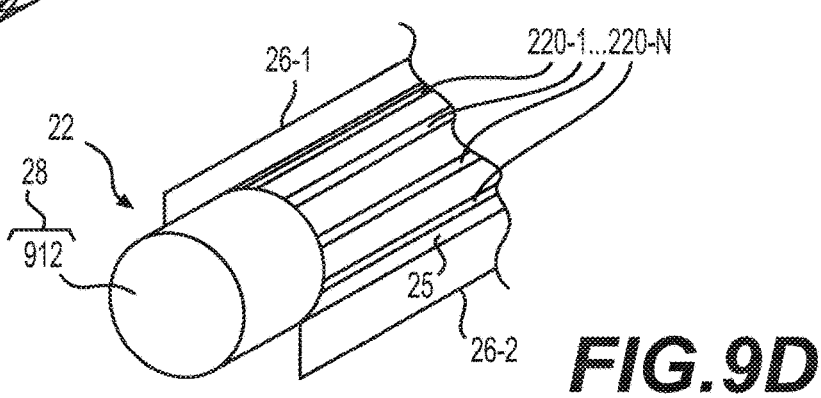

Referring to FIG. 9D, a vaporizer assembly 22 may include a heating element 28 that includes a surface heater 912. The surface heater 912 may be positioned on an end of the channel structure 25. As shown in the example embodiments illustrated in FIG. 9D, the surface heater 912 maybe a surface heater that is in contact with the channel structure 25. The surface heater 912 may be configured to transfer heat to pre-vapor formulation carried in the open-microchannels via conduction through the channel structure 25.

In some example embodiments, if and/or when the open-microchannels 220-1 to 220-N extend to the end of the channel structure 25, the surface heater 912 may establish a terminus of the open-microchannels 2201- to 220-N at the end of the channel structure 25. Pre-vapor formulation drawn to the end of the channel structure 25 through the open-microchannels 220-1 to 220-N may be in contact with one or more portions of the surface heater 912. The surface heater 912 may transfer heat to the pre-vapor formulations based at least in part upon conduction between the surface heater 912 and the pre-vapor formulation at an interface between the surface heater 912 and the pre-vapor formulation at the end of the channel structure 25.

In some example embodiments, the surface heater 912 may be one or more of a planar heater, a conformal heater, a ring heater, some combination thereof, etc. A surface heater, including a conformal heater, planar heater, etc., may be a flexible heater. A flexible heater may be a thick film heater constructed of one or more thick films. A flexible heater may include one or more resistive traces arranged in a pattern of resistive traces on a substrate. The substrate may be a flexible substrate. The flexible heater may include one or more adhesive layers configured to bond the flexible heater to a surface, including a gel formulation surface. An adhesive layer may include a pressure sensitive adhesive (PSA) layer.

A thick film heater may be a printed thick film heater where a pattern of resistive traces included in the thick film heater is a pattern of an ink material printed on a film substrate layer. The ink material may include a resistive ink. The film may include a PSA layer applied to the substrate on which the ink is printed. The thick film heater may include another layer laminated to the substrate and ink layer with the PSA layer. In some example embodiments, a film layer includes a 0.05-inch thick thermoplastic or thermoset polymer substance, where the substance is configured to exhibit thermal conductivity while providing electrical insulation. For example, the film layer may be formed of polyester or polyimide. An additional layer of PSA may be applied to an exterior surface of the thick film heater, such that the thick film heater may be bonded directly to the channel structure 25, thereby enhancing thermal transfer between the heater 912 and the channel structure 25.

In some example embodiments, a thick film heater includes a substrate constructed from one or more of polyester, polyethylene, polyvinyl chloride, thermoset laminate, polyethylene napthalate, polyimide, silicone rubber, or some combination thereof. A thick film heater may include a PSA layer formed of one or more of acrylic materials or silicone materials. A thick film heater may have a minimum width of 6 mm. A thick film heater may have a dielectric strength of up to 1500 VAC. A thick film heater may have a watt density of up to 25 W/square inches. A thick film heater may have an operating voltage of up to about 277 VAC or 277 VDC. A thick film heater may have an overall maximum operating temperature of about 482 degrees Celsius.

In some example embodiments, a flexible heater includes one or more of a single-sided heater, a double-sided heater, a multi-layer heater, a rigid-flex heater, and some combination thereof. A single sided heater includes a single heating element layer, which may be a resistive trace. A double sided heater includes two heating element layers. A flexible heater may include a sculptured heating element, where a sculptured heating element has variable thickness through the heater structure. A sculptured heating element may have bare metal portions exposed from the heater structure. A rigid-flex heater includes at least one rigid layer and at least one flexible layer. A flexible heater may have a thickness of at least 0.004 inches. A flexible heater may include at least two parallel traces having different resistances. The parallel traces may be separately, selectively activated to provide different rates of heating. A flexible heater may have a bend radius that is about 10 times the thickness of the flexible heater. One or more heating elements in the flexible heater may be radiused resistive traces. Where a flexible heater includes multiple layers of parallel heating elements, the separate layers may have a staggered configuration, thereby providing augmented flexibility of the flexible heater.

In some example embodiments, a surface heater 912 includes a solid state heater. A solid state heater may include a heating element that is one or more sets of resistive traces. A solid state heater may be a ceramic solid state heater. A solid state heater may be constructed from a combination of platinum and at least one ceramic material. A solid state heater may have a three-dimensional heating element geometric structure. A solid state heater may include multiple separate heating elements. A solid state heater may include an aluminum nitride ceramic material. A solid state heater may include a ceramic material and one or more internal resistance traces. A resistance trace may be constructed from tungsten. A solid state heater may include Aluminum nitride (ALN) ceramic and tungsten. Where a solid state heater includes ALN and tungsten, the tungsten metal and ALN may be bonded via chemical bonding. An oxide phase may be inter-diffused between the ALN and Tungsten metal.

In some example embodiments, a surface heater 902, 912 may include one or more various heater shapes, including serpentine heaters, which may contact one or more surfaces of the channel structure 25.

Figure 10:
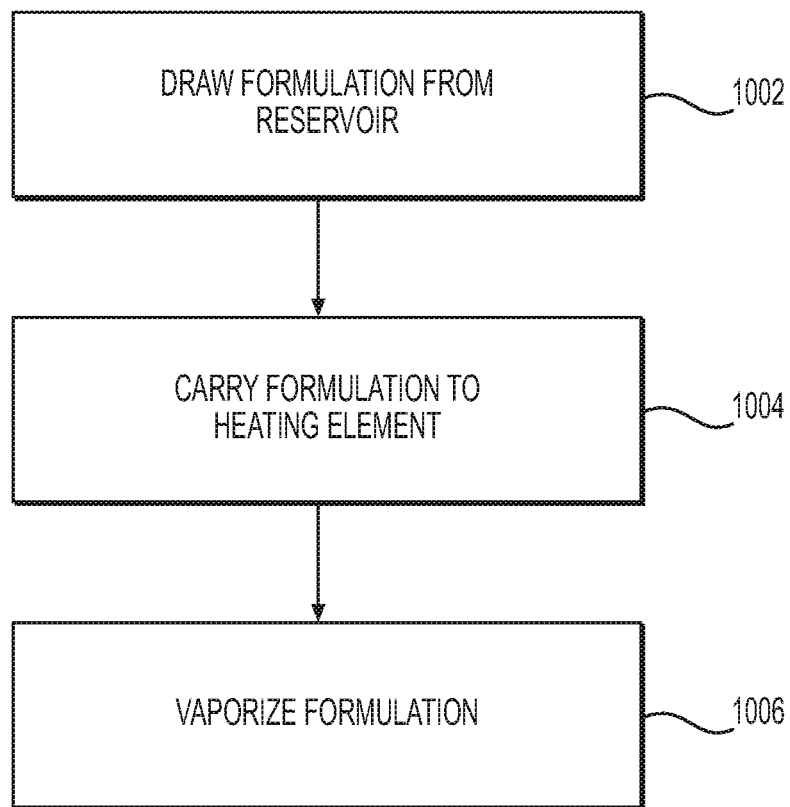
FIG. 10 is a flowchart illustrating a method for forming a vapor according to some example embodiments.

FIG. 10 is a flowchart illustrating a method for forming a vapor according to some example embodiments. The method may be implemented by a vaporizer assembly. Such a vaporizer assembly may include any of the example embodiments of vaporizer assemblies 22 included herein, including any of the example embodiments of vaporizer assemblies 22 illustrated in any of FIGS. 1-9C. However, the embodiments of vaporizer assembly that may implement the method illustrated in FIG. 10 are not limited to the example embodiments illustrated in one or more of FIGS. 1-9C.

As described above, a vaporizer assembly includes a reservoir that holds a pre-vapor formulation, a channel structure configured to draw pre-vapor formulation from the reservoir through one or more open-microchannels, and a heating element.

At 1002, the vaporizer assembly draws a pre-vapor formulation from a reservoir based on capillary action of the pre-vapor formulation through one or more micro-channels of the channel structure. The channel structure includes a channel surface with first and second portions. The first portion of the channel surface is in fluid communication with the reservoir interior and the second portion of the channel surface is external to the reservoir. The channel surface includes one or more open-microchannels extending between the first and second portions of the channel surface, such that portions of the open-microchannels extending through the first portion of the channel surface are in fluid communication with the reservoir interior. Portions of the open-microchannels extending through the first portion of the channel surface may receive pre-vapor formulation from the reservoir interior. The open-microchannels may draw pre-vapor formulation from the reservoir interior based on drawing the pre-vapor formulation through the open-microchannels from the first portion of the channel surface to the second portion of the channel surface.

At 1004, the vaporizer assembly carries pre-vapor formulation to the heating element. As described above, open-microchannels extending between the first and second portions of the channel surface may carry pre-vapor formulation from the reservoir. The open-microchannels may carry the pre-vapor formulation to at least a certain proximity of a heating element, such that the pre-vapor formulation in the open-microchannels may receive a sufficient amount of heat generated by the heating element to vaporize. In some example embodiments, one or more heating elements may be coupled to the open microchannels. The open-microchannels may carry pre-vapor formulation to physical contact with one or more heating elements.

At 1006, the vaporizer assembly vaporizes the pre-vapor formulation carried by the open-microchannels to the second portion of the channel surface. Such vaporization may include generating heat by the heating element, such that the pre-vapor formulation carried to the second portion of the channel surface is heated by the heating element and at least partially vaporizes. The vapor may be released from the open-microchannels.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A method, comprising:
   drawing a pre-vapor formulation from a plurality of reservoirs to a heating element through a plurality of open-microchannels, the plurality of open-microchannels including multiple sets of open-microchannels, each set of the plurality of open-microchannels being in fluid communication with a separate reservoir of the plurality of reservoirs, each set of the plurality of open-microchannels including a first portion and a second portion, the first portion being in fluid communication with the separate reservoir, and the second portion being coupled to the heating element; and
   vaporizing the pre-vapor formulations drawn to the heating element through the plurality of open-microchannels to form a vapor.

2. The method of claim 1, wherein the sets of open-microchannels of the plurality of open-microchannels are parallel.

3. The method of claim 1, wherein the plurality of reservoirs includes two or more reservoirs, and the plurality of open-microchannels includes two or more sets of open-microchannels.

4. The method of claim 1, wherein the open-microchannels of the plurality of open-microchannels have trapezoidal channel cross-sections.

5. The method of claim 1, wherein at least one of the sets of open-microchannels includes a hydrophilic layer.

6. The method of claim 1, wherein the heating element includes a surface heater.

7. The method of claim 1, wherein at least one of the plurality of reservoirs includes a sealing element configured to substantially seal an interface between the at least one of the plurality of reservoirs and the second portion of at least one of the sets of open-microchannels.

8. A method, comprising:
   drawing a pre-vapor formulation from a plurality of reservoirs to a heating element through a channel structure, the channel structure having a tubular structure and including multiple sets of open-microchannels extending axially along an outer surface of the tubular structure, each set of open-microchannels being in fluid communication with a separate reservoir of the plurality of reservoirs, each set of open-microchannels including a first portion and a second portion, the first portion being in fluid communication with the separate reservoir, and the second portion being coupled to the heating element; and
   vaporizing the pre-vapor formulations drawn to the heating element through the multiple sets of open-microchannels to form a vapor.

9. The method of claim 8, wherein the channel structure is a molded structure.

10. The method of claim 8, wherein the open-microchannels have trapezoidal channel cross-sections.

11. The method of claim 8, wherein the channel structure includes a hydrophilic layer on an outer layer of the tubular structure.

12. The method of claim 8, wherein the heating element includes a surface heater.

\* \* \* \* \*